United States Patent

Barbier et al.

Patent Number: 6,153,605
Date of Patent: Nov. 28, 2000

[54] ARYLSECOCHOLADIENE DERIVATIVES

[75] Inventors: Pierre Barbier, Rixheim, France; Franz Bauer, Reinach; Peter Mohr, Basel, both of Switzerland; Marc Muller, Saint-Louis, France; Wolfgang Pirson, Weil am Rhein, Germany

[73] Assignee: Hoffman-La Roche Inc., Nutley, N.J.

[21] Appl. No.: 09/061,381

[22] Filed: Apr. 16, 1998

[30] Foreign Application Priority Data

Apr. 21, 1997 [EP] European Pat. Off. .............. 97106547

[51] Int. Cl.⁷ .............................. A61K 3/59; C07C 401/00
[52] U.S. Cl. ............................................. 514/167; 552/653
[58] Field of Search .............................. 552/653; 514/167

[56] References Cited

U.S. PATENT DOCUMENTS

| | | |
|---|---|---|
| 5,447,924 | 9/1995 | Bretting . |
| 5,817,648 | 10/1998 | Kutner et al. ............................ 514/167 |
| 5,843,928 | 12/1998 | Deluca et al. .......................... 514/167 |
| 5,945,410 | 8/1999 | Deluca et al. .......................... 514/167 |

FOREIGN PATENT DOCUMENTS

| | | |
|---|---|---|
| WO 91/09841 | 7/1991 | WIPO . |
| WO 91/15475 | 10/1991 | WIPO . |
| WO 95/17197 | 6/1995 | WIPO . |

OTHER PUBLICATIONS

Grue–Soerensen, et al. Proc. Workshop, Vitamin D, vol. 9, 1994 pp. 75–76.

*Primary Examiner*—Barbara Badio
*Attorney, Agent, or Firm*—George W. Johnston; Patricia S. Rocha-Tramaloni; Robert A. Silverman

[57] ABSTRACT

Compounds of formula (I)

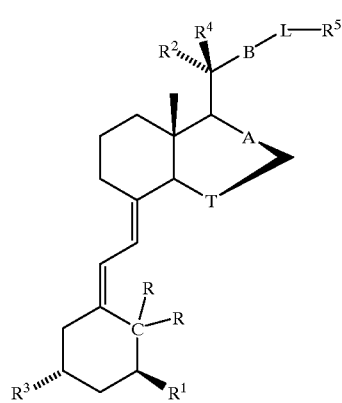

as defined by the specification. The compounds are useful in the treatment or prevention of vitamin D dependent disorders, particularly psoriasis, basal cell carcinomas, disorders of keratinization and keratosis, leukemia, osteoporosis, hyperparathyroidism accompanying renal failure, transplant rejection and graft vs. host disease.

31 Claims, No Drawings

ARYLSECOCHOLADIENE DERIVATIVES

BACKGROUND OF THE INVENTION

The term "vitamin D dependent disorders" refers to disorders which can be treated or prevented by the administration of compounds having vitamin D activity, such as vitamin $D_3$ or derivatives, in particular hydroxylated derivatives thereof, e.g. calcitriol or calcipotriol. Examples of such disorders are hyperproliferative skin diseases such as psoriasis, basal cell carcinomas, disorders of keratinization and keratosis; neoplastic diseases such as leukemia; disorders of the sebaceous glands such as acne and seborrhoic dermatitis; osteoporosis; hyperparathyroidism accompanying renal failure; and diseases which require modulation of the immune system, such as transplant rejection and graft vs. host disease.

However, vitamin D activity is often coupled with an undesirable level of toxicity. It is important to obtain compounds that have vitamin D activity sufficient to combat vitamin D dependent disorders, which have toxicity as low as possible compatible with activity.

SUMMARY OF THE INVENTION

The invention relates to compounds of formula (I)

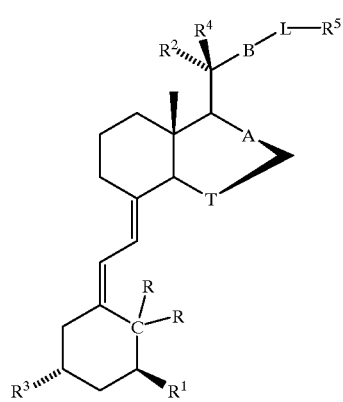

I wherein
A is a single or double bond,
B is a group $CH_2CH_2$, CH=CH or C≡C,
T is a group $CH_2$ or $CH_2CH_2$,
$R^1$ and $R^3$ are H or OH,
C(R,R) is $CH_2$ or C=$CH_2$,
$R^2$ is $CH_3$ and $R^4$ is H, or $R^2$ is H and $R^4$ is $CH_3$,
L is phenyl and $R^5$ is OH or $C(C_{1-4}\text{-alkyl})_2OH$, or L—$R^5$ is 2-furyl which is 5-substituted by $C(C_{1-4}\text{-alkyl})_2OH$, with the proviso that when L is phenyl, A is a single bond, B is C≡C, T is $CH_2$, each $R^1$ and $R^3$ are OH, C(R,R) is C=$CH_2$, $R^2$ is $CH_3$, $R^4$ is H, and $R^5$ is $C(CH_3)_2OH$, then $R^5$ is in the ortho or para position. These compounds are secocholadiene derivatives, preferably 24-nor-secochola-5,7-diene derivatives.

The compounds of this invention have vitamin D activity combined with low toxicity that make them particularly suitable for treatment and prevention of vitamin D disorders, especially those disorders related to hyperproliferative skin disorders such as psoriasis, basal cell carcinoma, keratinization and keratosis.

The present invention furthermore relates to a process for the preparation of the compound of formula I, pharmaceutical compositions containing the compound of formula I, and the use of the compound of formula I for the treatment of vitamin D dependent disorders and for the manufacture of pharmaceutical compositions for the treatment of vitamin D dependent disorders.

DETAILED DESCRIPTION OF THE INVENTION

The compounds of this invention are compounds of formula (I)

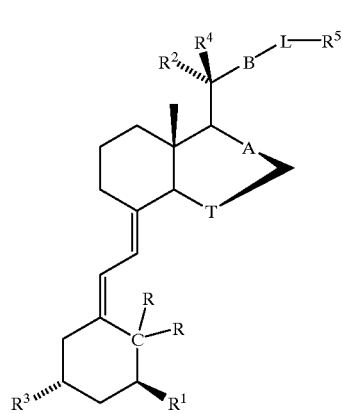

I wherein A is a single or double bond; B is $CH_2CH_2$, CH=CH, or C≡C; T is $CH_2$ or $CH_2CH_2$; $R^1$ and $R^3$ are H or OH; C(R,R) is $CH_2$ or C=$CH_2$; $R^2$ is $CH_3$ and $R^4$ is H, or $R^2$ is H and $R^4$ is $CH_3$; L is phenyl and $R^5$ is OH or $C(C_{1-4}\text{-alkyl})_2OH$ or L—$R^5$ is 2-furyl which is 5-substituted by $C(C_{1-4}\text{-alkyl})_2OH$, with the proviso that when L is phenyl, A is a single bond, B is C≡C, T is $CH_2$, $R^1$ and $R^3$ are OH, C(R,R) is C=$CH_2$, $R^2$ is $CH_3$, $R^4$ is H, and $R^5$ is $C(CH_3)_2OH$, then $R^5$ is in the ortho or para position. Thus it is understood that for any compound of this invention for which L is phenyl or A is a single bond or B is C≡C or T is $CH_2$ or $R^1$ is OH or $R^3$ is OH or C(R,R) is C=$CH_2$ or $R^2$ is $CH_3$ or $R^4$ is H or $R^5$ is $C(CH_3)_2OH$, then the proviso may apply if all the other limitations are also present. It is also understood that compounds of formula I may have any single characteristic described below or may have two or more such characteristics in any combination.

$C_{1-4}$ alkyl means any alkyl group having one to four carbons, branched or unbranched. Preferred $C_{1-4}$ alkyl groups are straight-chain alkyl groups such as ethyl, propyl, butyl, and especially methyl.

In any compound of this invention, A may be a single bond, $R^3$ may be OH, or T may be $CH_2$. Certain preferred compounds combine any two or all three of these characteristics, for example compounds of formula Ia where A is a single bond, $R^3$ is OH, and T is $CH_2$.

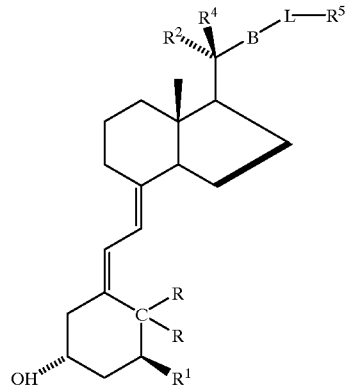

Ia while B, $R^1$, $R^2$, $R^4$; C(R,R), L and $R^5$ are as in formula I.

Compounds of formula Ia include those of formula Ib,

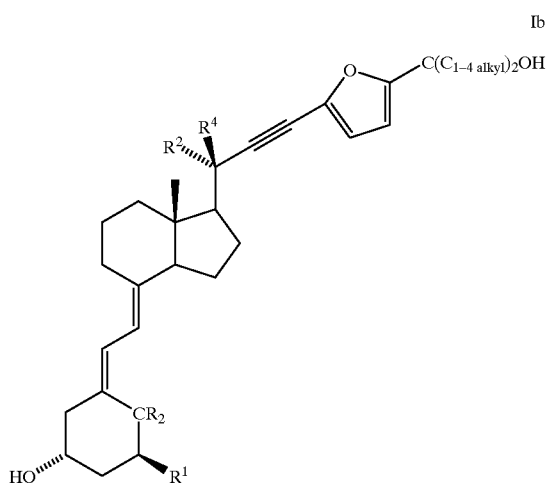

Ib where A is a single bond, B is C≡C, $R^3$ is OH, T is $CH_2$, L is 2-furyl which is 5 substituted by $C(C_{1-4}\ alkyl)_2OH$, while $R^1$, $R^2$, $R^4$, and C(R,R) are as in formula I. In a preferred compound of formula Ib, $R^2$ is $CH_3$ and $R^4$ is H. In an especially preferred compound, $C(C_{1-4}\ alkyl)_2OH$ is $C(CH_3)_2OH$. An example of such a compound is (7E)-(1R, 3R)-23-[5-(1-hydroxy-1-methyl-ethyl)-furan-2-yl]-19,24-dinor-9,10-seco-chola-5,7-dien-22-yne-1,3-diol.

Further compounds of formula Ia are depicted in formula Ic, where A is a single bond, $R^3$ is OH, T is $CH_2$ and L is phenyl, while

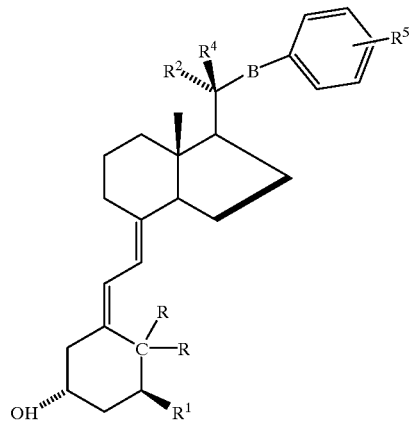

Ic

B, C(R,R), $R^1$, $R^2$, $R^4$, and $R^5$ are as in formula I.

In particular compounds of formula Ic, B may be $CH_2CH_2$, CH=CH, or C≡C, $R^5$ may be $C(CH_3)_2OH$ or OH. $R^1$ may be OH. $R^2$ and $R^4$ may each be H or $CH_3$ but not at the same time. In preferred compounds, B is $CH_2CH_2$ or C≡C, $R^5$ is $C(CH_3)_2OH$ or OH, $R^1$ is OH, and $R^2$ and $R^4$ are H and $CH_3$ or $CH_3$ and H.

Preferred compounds of formula I have L as phenyl. In such compounds, $R^5$ is preferably $C(CH_3)_2OH$ and $R^3$ may be OH. Further such compounds are depicted in formula Id, where A is a single bond, B is C≡C, $R^3$ is OH, L is phenyl, and $R^5$ is $C(CH_3)_2OH$,

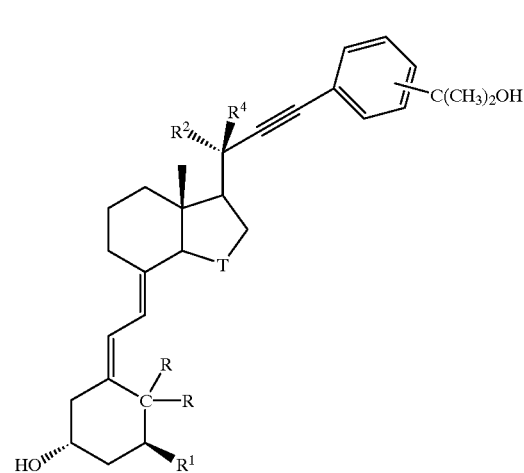

Id while T, $R^1$, C(R,R), $R^2$ and $R^4$ are as in formula I. In preferred compounds T may be $CH_2CH_2$ or $CH_2$ and $R^1$ may be OH. An example of such a compound is (7E)-(1R, 3R,20R)-23-[2-(1-Hydroxy-1-methyl-ethyl)-phenyl)-19,24-dinor-9,10-seco-chola-5,7-dien-22-yne-1,3-diol.

In other compounds of this invention where L is phenyl, $R^5$ is $C(CH_3)_2OH$, and $R^3$ is OH, B may be $CH_2CH_2$ or C≡C, and $R^1$ may be OH. Examples of such compounds are (7E)-(1R,3R)-23-[2-(1-Hydroxy-1-methyl-ethyl)-phenyl]-19,24-dinor-9,10-seco-chola-5,7-dien-1,3-diol, (7E)-(1R,3R)-23-[2-(1-hydroxy-1-methyl-ethyl)-phenyl]-19,24-dinor-9,10-seco-chola-5,7-dien-22-yne-1,3-diol, (7E)-(1R,3R)-23-[3-(1-hydroxy-1-methyl-ethyl)-phenyl]-19,24-dinor-9,10-seco-chola-5,7-dien-1,3-diol, (5Z,7E)-(1S,3R,20R)-23-[3-(1-hydroxy-1-methyl-ethyl)-phenyl)-24-nor-9,10-seco-chola-5,7,10(19)-trien-22-yne-1,3-diol, (5Z,7E)-(1S,3R,20R)-23-[2-(1-hydroxy-1-methyl-ethyl)-phenyl)-24-nor-9,10-seco-chola-5,7,10(19)-trien-22-yne-1,3-diol, (7E)-(1R,3R,20S)-23-[3-(1-hydroxy-1-methyl-ethyl)-phenyl)-19,24-dinor-9,10-seco-chola-5,7-dien-1,3-diol, (7E)-(1R,3R)-23-[2-(1-hydroxy-1-methyl-ethyl)-phenyl]-D-homo-19,24-dinor-9,10-seco-chola-5,7,17-trien-22-yne-1,3-diol, (5Z,7E)-(1S,3R,21R)-23-[2-(1-hydroxy-1-methyl-ethyl)-phenyl]-D-homo-24-nor-9,10-seco-chola-5,7,10(19)-trien-22-yne-1,3-diol.

This invention is also directed to compounds which are intermediates for the compounds of formula (I) described above. Thus, this invention includes compounds of formulae II–VI as described below:

Compounds of formula (II):

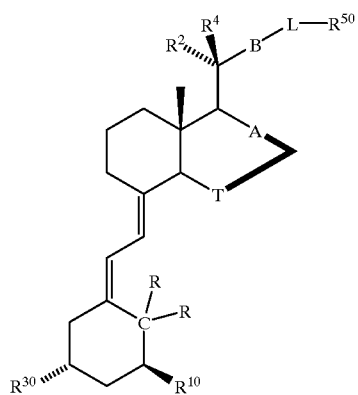

Compounds of formula IV:

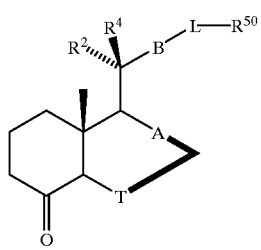

Compounds of formula IVa:

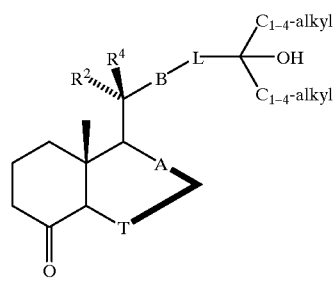

Compounds of formula V:

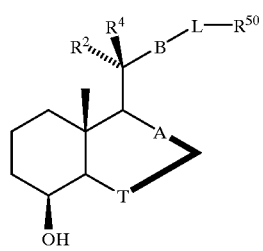

In the above compounds of formulae II, IV, IVa, and V, A, B, T, R, $R^2$, $R^4$ and L are as in claim 1, $R^{10}$ and $R^{30}$ are H or $OSi(CH_3)_2$-tert-butyl and $R^{50}$ is $OSi(CH_3)_3$, $OSi(CH_3)_2$-tert-butyl or $C(C_{1-4}$-alkyl$)2OSi(CH_3)_3$.

This invention is directed to a process for preparing the compounds of formula I which comprises cleaving the silyl-protecting group(s) contained in a compound of formula

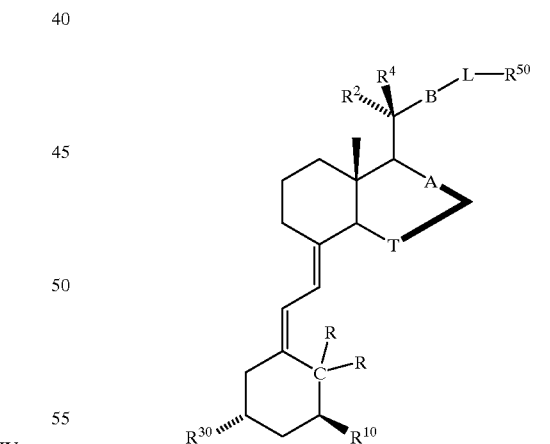

wherein A, B, T, R, $R^2$, $R^4$ and L are as in claim 1, $R^{10}$ and $R^{30}$ are H or $OSi(CH_3)_2$-tert-butyl and $R^5$ is $OSi(CH_3)_3$, $OSi(CH_3)_2$-tert-butyl or $C(C_{1-4}$-alkyl$)_2OSi(CH_3)_3$.

The compounds of formula I can accordingly be obtained by cleavage of the silyl-protecting group(s) contained in a compound of formula

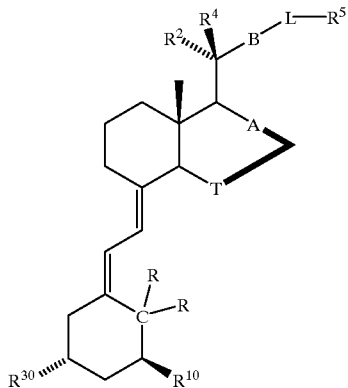

as defined above. The intermediates of formula II hereinabove and those of formulae IV, IVa and V are novel and as such are a further object of the present invention.

By silyl protecting group is meant a group forming a silylether with the hydroxy group to be protected, such silyl protecting groups are for example —Si(alkyl)$_3$, especially —Si(CH$_3$)$_3$ or —Si(alkyl)$_2$-tert-butyl, especially —Si(CH$_3$)$_2$-tert-butyl.

In the synthetic schemes provided below, the basic reactions described (e.g. cleavage, coupling, oxidation, silylation, hydrogenation, Wittig and ene reactions, and the like) will be familiar to a skilled person, who will understand how to perform such reactions in the customary way using reagents and starting materials provided herein to obtain the compounds of this invention. The reagents required herein (e.g. various solvents, catalysts, and reagents for the basic reactions described), and starting materials of Scheme 1 and Scheme 2, from which all the compounds are ultimately derived, are well known materials which are readily obtained from chemical suppliers or synthesized by well known methods.

The cleavage can be effected by tetrabutylammonium fluoride (TBAF) in a solvent such as THF.

The compounds of formula II are obtained by coupling a phosphinoxyde of formula

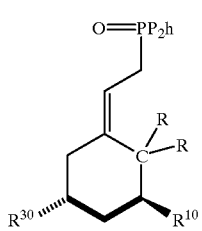

with a ketone of formula

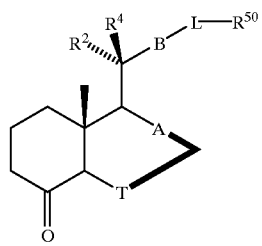

The coupling can be effected by reacting a solution of the phosphinoxyde in THF with butyl lithium and then with a ketone IV at −78° C.

The ketones IV wherein $R^{50}$ is $C(C_{1-4}\text{-alkyl})_2OSi(CH_3)_3$ can be obtained by oxidation followed by silylation of the diols of the formula

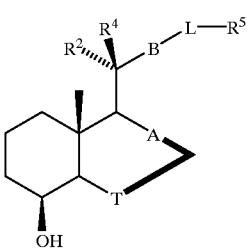

wherein $R^5$ is $C(C_{1-4}\text{-alkyl})_2OH$.

The products of this oxidation are hydroxy-ketones of the formula IVa

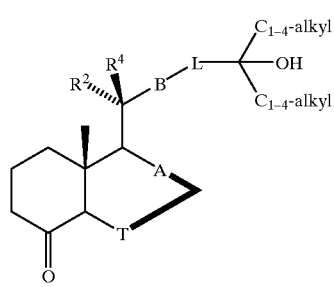

The oxidation can be effected in DMF or in CH$_2$Cl$_2$ with pyridinium dichromate (PDC). The silylation can be carried out by reacting the ketone intermediate in THF or in CH$_2$Cl$_2$ at 0° C. with 1-trimethylsilyl-imidazol, optionally in mixture with imidazol and trimethylsilylchloride.

The ketones IV wherein $R^{50}$ is OSi(CH$_3$)$_3$ or OSi(CH$_3$)$_2$-tert-butyl can be obtained by silylation of the alcohol-phenols of formula V, wherein $R^5$ is OH, followed by oxidation.

The silylation of the phenolic hydroxy can be effected in DMF or in CH$_2$Cl$_2$ with tert-butyldimethylsilylchloride and imidazol. The oxidation can be carried out in DMF with PDC.

The diols V, wherein $R^5$ is $C(C_{1-4}\text{-alkyl})_2OH$, can be obtained by reacting the alcohol-esters of formula

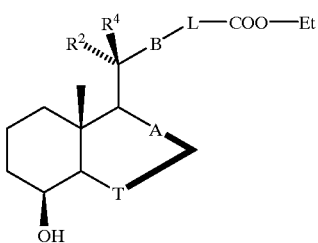

VI with methylmagnesiumchloride in THF at 0° C.

The alcohol-phenols V wherein L is phenyl, $R^5$ is OH and B is C≡C or CH=CH can be obtained by coupling the alcohols of formula VII or VIII

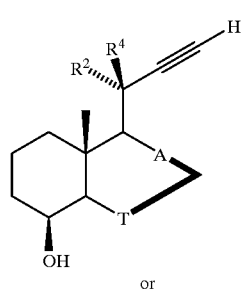

VII or

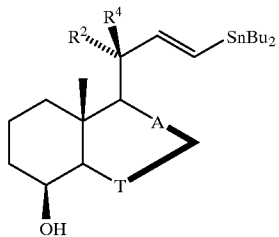

VIII with iodophenol in the presence of a palladium catalyst and copper-(I)-iodide in piperidine or in 2,2,6,6-tetramethylpiperidine.

Similarly, alcohol-esters of formula VI, wherein B is C≡C or CH=CH can be obtained by reacting a solution of the alcohols of formula VII or VIII with a halogenide of formula Hal-L—COOEt, such as ethyliodobenzoat, in the presence of bis(triphenylphosphin)palladium(II)-dichloride and copper-(I)-iodide.

Alcohol-esters VI wherein B is $CH_2CH_2$ can be obtained by catalytic hydrogenation, e.g. over Pd/C in ethanol, of the corresponding alcohol-esters VI wherein B is C≡C.

The compounds VIII are obtained from compounds VII by reaction in toluene with tributyltinhydride and azobisisobutyronitrile.

The compounds of formula VII are obtained by deprotection of corresponding compounds of formula

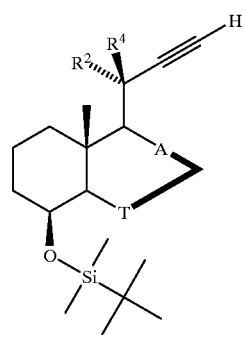

IX e.g. in THF with hydrofluoric acid or dry TBAF.

A compound of formula IX can be reacted with a halogenide of formula Hal-L—COOEt, such as 2-bromo-furan-5-ylcarboxylic acid ethyl ester, in the presence of bis-(triphenylphosphin)-palladium(II)-dichloride and copper(I)-iodide. The obtained ester can be deprotected, e.g. in THF with hydrofluoric acid, to the corresponding alcohol ester of formula VI.

The compounds of formula IX are obtained from compounds of formula

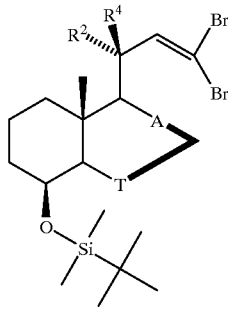

X by reaction in THF at −78° C. with butyllithium.

The compounds of formula X are obtained from aldehydes of formula

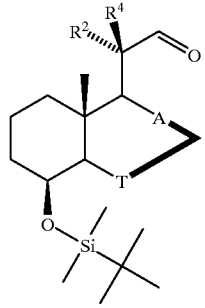

XI by reaction with tetrabromomethane in dichloromethane in the presence of triphenylphosphine at −20° C.

The aldehydes of formula XI can be obtained by oxidation of the alcohols of formula XII

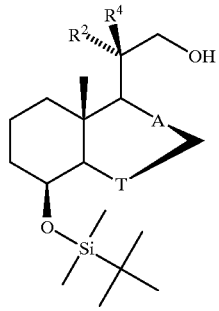

XII e.g. in dichloromethane, with catalytic amounts of tetrapropyl ammonium perruthenate (TPAP) in the presence of a molecular sieve and with N-methyl morpholine oxide as cooxydant, or with oxalyl chloride, DMSO and $NEt_3$ in $CH_2Cl_2$.

An ether-alcohol XII with the non-natural configuration ($R^2$=H, $R^4$=$CH_3$) can be obtained by epimerization of the corresponding aldehyde XI with natural configuration, with 1,5-diazabicyclo[4.3.0]non-5-en (DBN) in THF, followed by reduction with sodium borohydride and chromatographic separation of the desired alcohol XII.

Compounds of formula XII wherein T is $CH_2CH_2$ can be prepared as described in the U.S. patent application Ser. No. 08/993851 incorporated by reference as set forth in formula Scheme 1 below:

According to Scheme 1, compound (1) [Synthesis 957 (1993)] is reduced to yield the equatorial alcohol (2), which is transformed to (4) via the thiocarbamate (3). Compound (4) can be hydroborated to yield (5). Oxydation of the alcohol, e.g., with pyridiniumchlorochromate or TPAP and equilibration with potassium-t-butoxide yields (6), which can be reduced to give compound (7). Acetylation of (7) and cleavage of the tert-butyl ether function yields (8) which is oxidized and deacylated to yield ketoalcohol (9). For build-up of the vitamin $D_3$ side chain the alcohol group of (9) is suitably protected, e.g., by a silyl ether protecting group Z, preferably the tert-butyl-dimethyl-silyl group, to obtain (10).

The ketone (10) is converted by a Wittig reaction into compound (11) from which (12) is obtained by an ene reaction with paraformaldehyde and dimethylaluminum chloride, or with paraformaldehyde and $BF_3.Et_2O$. Catalytic hydrogenation of (12) gives (13).

Scheme 1

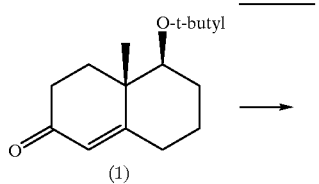

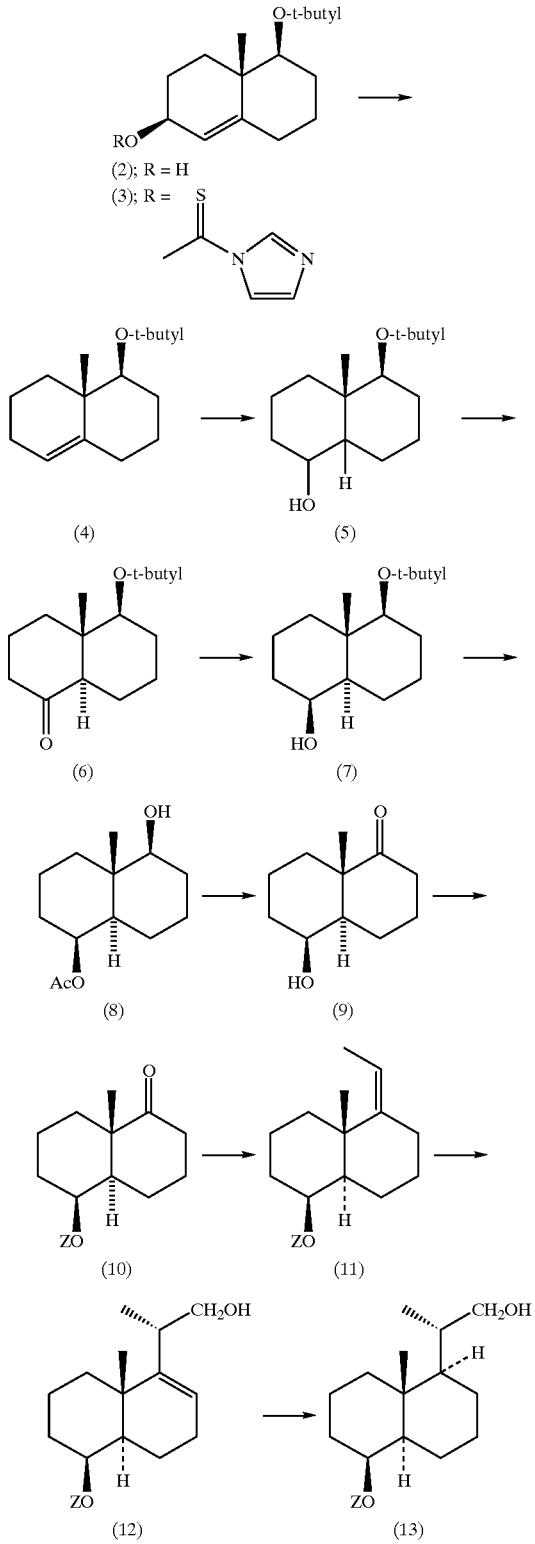

The phosphinoxydes of formula III are known or can be obtained in a manner analogous to the known compounds. Thus, those wherein C(R,R) is $CH_2$ can be prepared as shown in formula Scheme 2 below:

Scheme 2

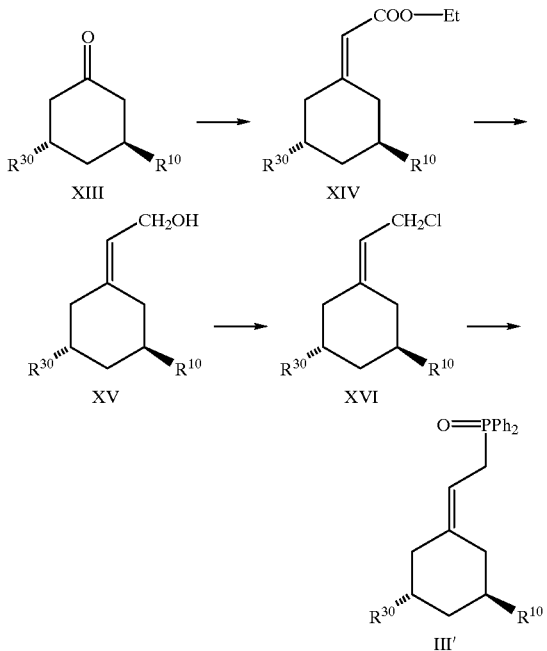

According to Scheme 2, the ketone XIII is converted by a Peterson reaction into the ester XIV from which the alcohol XV is obtained by reduction. Reaction of XV with N-chlorosuccinimide in the presence of dimethylsulphur gives the chloride XVI. Reaction of XVI with diphenylphosphine-lithium and work-up with 5% $H_2O_2$ in ethyl acetate gives the phosphinoxide III.

The following Examples 1–33 describe the preparation of the compounds of formula I in more detail. The Examples are provided by way of illustration and are not intended to limit the invention in any way.

In Examples 1 to 26, compounds of formula I were obtained by cleavage of the silyl-protecting group(s) in compounds of formula II:

EXAMPLE 1

(7E,22E)-(1R,3R)-23-[4-(1-Hydroxy-1-methyl-ethyl)-phenyl]-19,24-dinor-9,10-seco-chola-5,7,22-triene-1,3-diol from (7E,22E)-(1R,3R)-1,3-Bis-(tert-butyldimethyl-silanyloxy)-23-[4-(1-methyl-1-trimethylsilanyloxy-ethyl)-phenyl]-19,24-dinor-9,10-seco-chola-5,7,22-triene.

MS: $(M)^+$ 464

IR: $cm^{-1}$ 3432; 2931; 2878; 1452; 1371; 1257; 1214; 1169; 1134; 1094; 1050; 967; 863; 813.

EXAMPLE 2

(7E,22E)-(1R,3R)-23-[2-(1-Hydroxy-1-methyl-ethyl)-phenyl]-19,24-dinor-9,10-seco-chola-5,7,22-triene-1,3-diol from (7E,22E)-(1R,3R)-1,3-Bis-(tert-butyldimethyl-silanyloxy)-23-[2-(1-methyl-1-trimethylsilanyloxy-ethyl)-phenyl]-19,24-dinor-9,10-seco-chola-5,7,22-triene.

MS: $(M)^+$ 464

IR: $cm^{-1}$ 3424; 2947; 2870; 1621; 1444; 1371; 1048; 974; 757.

EXAMPLE 3

(7E,22E)-(1R,3R)-23-(3-Hydroxy-phenyl)-19,24-dinor-9,10-seco-chola-5,7,22-triene-1,3-diol from (7E,22E)-(1R,3R)-1,3-Bis-(tert-butyl-dimethyl-silanyloxy)-23-[3-(1-methyl-1-trimethylsilanyloxy-ethyl)-phenyl]-19,24-dinor-9,10-seco-chola-5,7,22-triene.

MS: $(M)^+$ 422

IR: $cm^{-1}$ 3419; 3042; 2947; 2869; 1613; 1585; 1451; 1375; 1286; 1260; 1229; 1156; 1044; 970; 777.

EXAMPLE 4

(7E,22E)-(1R,3R)-23-[3-(1-Hydroxy-1-methyl-ethyl)-phenyl]-19,24-dinor-9,10-seco-chola-5,7,22-triene-1,3-diol from (7E,22E)-(1R,3R)-1,3-Bis-(tert-butyldimethyl-silanyloxy)--23-[3-(1-methyl-1-trimethylsilanyloxy-ethyl)-phenyl]-19,24-dinor-9,10-seco-chola-5,7,22-triene.

MS: $(M)^+$ 464

IR: $cm^{-1}$ 3431; 2947; 2871; 1627; 1050; 970; 702.

EXAMPLE 5

(7E)-(1R,3R)-23-[2-(1-Hydroxy-1-methyl-ethyl)-phenyl]-19,24-dinor-9,10-seco-chola-5,7-dien-1,3-diol from (7E)-(1R,3R)-1,3-Bis-(tert-butyldimethyl-silanyloxy)-23-[2-(1-methyl-1-trimethylsilanyloxy-ethyl)-phenyl]-19,24-dinor-9,10-seco-chola-5,7-diene.

MS: $(M)^+$ 466

IR: $cm^{-1}$ 3422; 2944; 2871; 1619; 1442; 1376; 1047; 761

EXAMPLE 6

(7E)-(1R,3R)-23-[2-(1-Hydroxy-1-methyl-ethyl)-phenyl]-19,24-dinor-9,10-seco-chola-5,7-dien-22-yne-1,3-diol from (7E)-(1R,3R)-1,3-Bis-(tert-butyldimethyl-silanyloxy)-23-[2-(1-methyl-1-trimethylsilanyloxy-ethyl)-phenyl]-19,24-dinor-9,10-seco-chola-5,7-diene-22-yne.

MS: $(M)^+$ 462

IR: $cm^{-1}$ 3415; 1931; 2872; 1623; 1441; 1362; 1046; 759.

EXAMPLE 7

(7E)-(1R,3R)-23-[3-(1-Hydroxy-1-methyl-ethyl)-phenyl]-19,24-dinor-9,10-seco-chola-5,7-dien-1,3-diol from (7E)-(1R,3R)-1,3-Bis-(tert-butyl-dimethyl-silanyloxy)-23-[3-(1-methyl-1-trimethylsilanyloxy-ethyl)-phenyl]-19,24-dinor-9,10-seco-chola-5,7-diene.

MS: $(M)^+$ 466

IR: $cm^{-1}$ 3409; 2944; 2870; 1620; 1442; 1376; 1048; 793; 709.

EXAMPLE 8

(7E,)-(1R,3R)-23-[3-(1-Hydroxy-1-methyl-ethyl)-phenyl]-19,24-dinor-9,10-seco-chola-5,7-dien-22-yne-1,3-diol from (7E)-(1R,3R)-1,3-Bis-(tert-butyldimethyl-silanyloxy)-23-[3-(1-methyl-1-trimethylsilanyloxy-ethyl)-phenyl]-19,24-dinor-9,10-seco-chola-5,7-diene-22-yne.

MS: $(M)^+$ 462

IR: $cm^{-1}$ 3410; 2931; 2872; 1619; 1451; 1415; 1366; 1309; 1272; 1217; 1174; 1142; 1081; 1047; 975; 795; 700.

EXAMPLE 9

(7E)-(1R,3R)-23-[4-(1-Hydroxy-1-methyl-ethyl)-phenyl]-19,24-dinor-9,10-seco-chola-5,7-dien-1,3-diol from (7E)-(1R,3R)-1,3-Bis-(tert-butyldimethyl-silanyloxy)-23-[4-(1-methyl-1-trimethylsilanyloxy-ethyl)-phenyl]-19,24-dinor-9,10-seco-chola-5,7-diene.

MS: $(M)^+$ 466

IR: $cm^{-1}$ 3396; 2944; 2870; 1617; 1511; 1450; 1409; 1376; 1258; 1215; 1170; 1145; 1118; 1048; 976; 954; 863; 813.

EXAMPLE 10

(7E,)-(1R,3R)-23-[4-(1-Hydroxy-1-methyl-ethyl)-phenyl]-19,24-dinor-9,10-seco-chola-5,7-dien-22-yne-1,3-diol from (7E)-(1R,3R)-1,3-Bis-(tert-butyldimethyl-silanyloxy)-23-[4-(1-methyl-1-trimethylsilanyloxy-ethyl)-phenyl]-19,24-dinor-9,10-seco-chola-5,7-dien-22-yne.

MS: (M)$^+$ 462

IR: cm$^{-1}$ 3422; 2966; 2931; 2872; 2238; 1619; 1503; 1451; 1365; 1308; 1255; 1217; 1172; 1142; 1110; 1092; 1047; 958; 862; 836.

EXAMPLE 11

(7E,)-(1R,3R)-23-(3-Hydroxy-phenyl)-19,24-dinor-9,10-seco-chola-5,7-dien-22-yne-1,3-diol from (7E)-(1R,3R)-1,3-Bis-(tert-butyldimethyl-silanyloxy)-23-[3-(tert-butyldimethyl-silanyloxy)-phenyl]-19,24-dinor-9,10-seco-chola-5,7-dien-22-yne.

MS: (M)$^+$ 420

IR: cm$^{-1}$ 3345; 2931; 2873; 2226; 1578; 1445; 1347; 1286; 1183; 1079; 1042; 977; 871; 782; 692.

EXAMPLE 12

(7E,)-(1R,3R)-23-(3-Hydroxy-phenyl)-19,24-dinor-9,10-seco-chola-5,7-dien-1,3-diol from (7E)-(1R,3R)-1,3-Bis-(tert-butyldimethyl-silanyloxy)-23-[3-(tert-butyldimethyl-silanyloxy)-phenyl]-19,24-dinor-9,10-seco-chola-5,7-diene.

MS: (M)$^+$ 424

IR: cm$^{-1}$ 3434; 2945; 2870; 1591; 1454; 1376; 1272; 1234; 1155; 1045; 975; 781; 695.

EXAMPLE 13

(7E)-(1R,3R)-23-(4-Hydroxy-phenyl)-19,24-dinor-9,10-seco-chola-5,7-dien-22-yne-1,3-diol from (7E)-(1R,3R)-1,3-Bis-(tert-butyldimethyl-silanyloxy)-23-[4-(tert-butyldimethyl-silanyloxy)-phenyl]-19,24-dinor-9,10-seco-chola-5,7-dien-22-yne.

MS: (M)$^+$ 420

IR: cm$^{-1}$: 3429; 2932; 2872; 1609; 1511; 1263; 1218; 1044; 832.

EXAMPLE 14

(5Z,7E)-(1S,3R,20R)-23-[3-(1-Hydroxy-1-methyl-ethyl)-phenyl]-24-nor-9,10seco-chola-5,7,10(19)-trien-22-yne-1,3-diol from (5Z,7E)-(1S,3R,20R)-1,3-Bis-(tert-butyldimethyl-silanyloxy)-23-[3-(1-methyl-1-trimethyl-silanyloxy-ethyl)-phenyl]-24-nor-9,10-seco-chola-5,7,10 (19)-trien-22-yne.

MS: (M)$^+$ 474

IR: cm$^{-1}$: 3428; 2931; 2872; 2218; 1635; 1053; 897; 796; 700.

EXAMPLE 15

(7E)-(1R,3R,20R)-23-[3-(1-Hydroxy-1-methyl-ethyl)-phenyl]-19,24-dinor-9,10-seco-chola-5,7-dien-22-yne-1,3-diol from (7E)-(1R,3R,20R)-1,3-Bis-(tert-butyldimethyl-silanyloxy)-23-[3-(1-methyl-1-trimethylsilanyloxy-ethyl)-phenyl]-19,24-dinor-9,10-seco-chola-5,7-dien-22-yne.

MS: (M)$^+$ 462

IR: cm$^{-1}$: 3413; 2930; 2873; 2230; 1620; 1487; 1047; 866; 801; 703.

EXAMPLE 16

(5Z,7E)-(1S,3R,20R)-23-[2-(1-Hydroxy-1-methyl-ethyl)-phenyl)-24-nor-9,10-seco-chola-5,7,10(19)-trien-22-yne-1,3-diol from (5Z,7E)-(1S,3R,20R)-1,3-Bis-(tert-butyldimethyl-silanyloxy)-23-[2-(1-methyl-1-trimethyl-silanyloxy-ethyl)-phenyl]-24-nor-9,10-seco-chola-5,7,10 (19)-trien-22-yne.

MS: (M)$^+$ 474

IR: cm$^{-1}$: 3422; 2930; 2872; 1634; 1477; 1442; 1364; 1173; 1053; 954; 914; 859; 759.

EXAMPLE 17

(7E)-(1R,3R,20R)-23-[2-(1-Hydroxy-1-methyl-ethyl)-phenyl)-19,24-dinor-9,10-seco-chola-5,7-dien-22-yne-1,3-diol from (7E)-(1R,3R,20R)-1,3-Bis-(tert-butyldimethyl-silanyloxy)-23-[2-(1-methyl-1-trimethylsilanyloxy-ethyl)-phenyl]-19,24-dinor-9,10-seco-chola-5,7-dien-22-yne.

MS: (M)$^+$ 462

IR: cm$^{-1}$ 3417; 2930; 2872; 1620; 1445; 1363; 1307; 1230; 1173; 1119; 1046; 976; 953; 858; 759.

EXAMPLE 18

(5Z,7E)-(1S,3R,20S)-23-[3-(1-Hydroxy-1-methyl-ethyl)-phenyl]-24-nor-9,10-seco-chola-5,7,10(19)-trien-1,3-diol from (5Z,7E)-(1S,3R,20S)-1,3-Bis-(tert-butyldimethyl-silanyloxy)-23-[3-(1-methyl-1-trimethylsilanyloxy-ethyl)-phenyl]-24-nor-9,10-seco-chola-5,7,10 (19)-triene.

MS: (M)$^+$ 478

IR: cm$^{-1}$ 3425; 2930;2871; 1632; 1380; 1055; 957; 899; 708.

EXAMPLE 19

(7E)-(1R,3R,20S)-23-[3-(1-Hydroxy-1-methyl-ethyl)-phenyl]-19,24-dinor-9,10-seco-chola-5,7-dien-1,3-diol from (7E)-(1R,3R,20S)-i,3-Bis-(tert-butyldimethyl-silanyloxy)-23-[3-(1-methyl-1-trimethylsilanyloxy-ethyl)-phenyl]-19,24-dinor-9,10-seco-chola-5,7-diene.

MS: (M)$^+$ 466

IR: cm$^{-1}$ 3414; 2933; 2871; 1616; 1490; 1450; 1376; 1175; 1082; 1047; 978; 959; 798; 708.

EXAMPLE 20

(5Z,7E)-(1S,3R,20R)-23-(3-Hydroxy-phenyl)-24-nor-9,10-seco-chola-5,7,10(19)-trien-22-yne -1,3-diol from (5Z,7E)-(1S,3R,20R)-1,3-Bis-(tert-butyldimethyl-silanyloxy)-23-[3-(tert-butyldimethyl-silanyloxy)-phenyl]-24-nor-9,10-seco-chola-5,7,10(19)-triene-22-yne.

MS: (M)$^+$ 432

IR: cm$^{-1}$ 3415; 2945; 2872; 2232; 1612; 1595; 1579; 1446; 1286; 1189; 1051; 782; 688.

EXAMPLE 21

(7E)-(1R,3R,20R)-23-(3-Hydroxy-phenyl)-19,24-dinor-9,10-seco-chola-5,7-dien-22-yne -1,3-diol from (7E)-(1R,3R,20R)-1,3-Bis-(tert-butyldimethyl-silanyloxy)-23-[3(tert-butyldimethyl-silanyloxy)-phenyl]-19,24-dinor-9,10-seco-chola-5,7-diene -22-yne.

MS: (M)$^+$ 420

IR: cm$^{-1}$ 3422; 2932; 2873; 2240; 1611; 1594; 1579; 1448; 1287; 1184; 1044; 872; 788; 691.

EXAMPLE 22

(5Z,7E,22E)-(1S,3R,20S)-23-(3-Hydroxy-phenyl)-24-nor-9,10-seco-chola-5,7,10(19)-22-tetraene-1,3-diol from (5Z,7E,22E)-(1S,3R,20S)-1,3-Bis-(tert-butyldimethylsilanyloxy)-23-[3-(tert-butyldimethyl-silanyloxy)-phenyl]-24-nor-9,10-seco-chola-5,7,10(19),22-tetraene.

MS: (M)$^+$ 434

IR: cm$^1$ 3432; 2950; 2869; 1612; 1586; 1451; 1282; 1258; 1153; 1052; 970; 957; 870; 773; 688.

EXAMPLE 23

(7E,22E)-(1R,3R,20S)-23-(3-Hydroxy-phenyl)-19,24-dinor-9,10-seco-chola-5,7,22 trien-1,3-diol from (7E,22E)-(1R,3R,20S)-1,3-Bis-(tert-butyldimethyl-silanyloxy)-23-[3-(tert-butyldimethyl-silanyloxy)-phenyl]-19,24-dinor-9,10-seco-chola-5,7,22-triene.

MS: (M)$^+$ 422

IR: cm$^{-1}$ 3422;2953; 2929; 2869; 1613; 1585; 1451; 1374; 1284; 1155; 1079; 1044; 972; 870; 777; 691.

EXAMPLE 24

(7E)-(1R,3R)-23-[5-(1-Hydroxy-1-methyl-ethyl)-furan-2-yl]-19,24-dinor-9,10-seco-chola-5,7-dien-22-yne-1,3-diol from (7E)-(1R,3R)-1,3-Bis-(tert-butyl-dimethyl-silanyloxy)-23-[5-(1-trimethylsilanyloxy-1-methyl-ethyl)-furan-2-yl]-19,24-dinor-9,10-seco-chola-5,7-diene-22-yne.

MS: (M)$^+$ 452

IR: cm$^{-1}$ 3345; 2954; 2922; 2855; 2240; 1617; 1534; 1456; 1377; 1366; 1305; 1262; 1200; 1189; 1169; 1149; 1119; 1080; 1047; 1024; 9781963; 940; 789.

EXAMPLE 25

(5Z,7E)-(1S,3R)-23-[5-(1-Hydroxy-1-methyl-ethyl)-furan-2-yl]-24-nor-9,10-chola-5,7,10(19)-trien-22-yne-1,3-diol from (5Z,7E)-(1 S,3R)-1,3-Bis-(tert-butyl-dimethyl-silanyloxy)-23-[5-(1-trimethylsilanyloxy-1-methyl-ethyl)-furan-2-yl]-24-nor-9,10-seco-chola-5,7,10(19)-trien-22-yne.

MS: (M)$^+$ 464

IR: cm$^{-1}$ 3360; 2934; 2880; 1538; 1453; 1380; 1366; 1309; 1264; 1203; 1183; 1170; 1148; 1121; 1052; 1023; 966; 899; 847; 791.

EXAMPLE 26

(5Z,7E)-(3S)-23-[5-(1-Hydroxy-1-methyl-ethyl)-furan-2-yl]-24-nor-9,10-seco-chola-5,7,10(19)-trien-22-yne-3-ol from (5Z,7E)-(3S)-3-(tert-Butyl-dimethyl-silanyloxy)-23-[5-(1-trimethylsilanyloxy-1-methyl-ethyl)-furan-2-yl]-24-nor-9,10-seco-chola-5,7,10(19)-trien-22-yne.

MS: (M)$^+$ 448

IR: cm$^{-1}$ 3360; 2940; 2880; 1540; 1443; 1380; 1367; 1267; 1203; 1172; 1150; 1122; 1052; 1028; 968; 947; 898; 870; 848; 791.

Typically, the product of formula II, (5Z,7E)-(1S,3R,20R)-1,3-Bis-(tert-butyldimethyl-silanyloxy)-23-[2-(1-methyl-1-trimethyl-silanyloxy-ethyl)-phenyl]-24-nor-9,10-seco-chola-5,7,10(19)-trien-22-yne was dissolved in a 1 molar solution of TBAF (tetra-butyl ammonium fluoride) in THF (2 ml; 2 mmol; 10 equivalents) and stirred over night at room temperature. The reaction mixture was then poured on chilled brine, extracted twice with ethyl acetate, washed twice with brine, dried over anhydrous sodium sulfate and the solvent was removed. After flash-chromatography (eluent: hexanes/isopropanol 73/27) the product of the above Example 16, (5Z,7E)-(1S,3R,20R)-23-[2-(1-Hydroxy-1-methyl-ethyl)-phenyl]-24-nor-9,10-seco-chola-5,7,10(19)-trien-22-yne-1,3-diol was obtained as a colorless foam (71 mg; yield 73%).

A) The following compounds of formula II were obtained from compounds of formula III and IV:

EXAMPLE 1A (7E,22E)-(1R,3R)-1,3-Bis-(tert-butyldimethyl-silanyloxy)-23-[4-(1-methyl-1-trimethylsilanyloxy-ethyl)-phenyl]-19,24-dinor-9,10-seco-chola-5,7,22-triene from (E)-(1R,3aR,7aR)-7a-Methyl-1-[(R)-1-methyl-3-[4-(1-methyl-1-trimethylsilanyloxy-ethyl)-phenyl]-prop-2-enyl]-octahydro-inden-4-one.

MS: (M)$^+$ 765

IR: cm$^1$ 4331; 2955; 2886; 2856; 1616; 1468; 1361; 1253; 1174; 1093; 1048; 917; 837; 775.

EXAMPLE 2A (7E,22E)-(1R,3R)-1,3-Bis-(tert-butyldimethyl-silanyloxy)-23-[2-(1-methyl-1-trimethylsilanyloxy-ethyl)-phenyl]-19,24-dinor-9,10-seco-chola-5,7,22-triene from (E)-(1R,3aR,7aR)-7a-Methyl-1-[(R)-1-methyl-3-[2-(1-methyl-1-trimethylsilanyloxy-ethyl)-phenyl]-allyl]-octahydro-inden-4-one.

MS: (M)$^+$ 765

IR: cm$^{-1}$ 3058; 2953; 2885; 2856; 1612; 1468; 1379; 1361; 1252; 1212; 1158; 1085; 1026; 960; 918; 836; 776; 697; 669.

EXAMPLE 3A (7E,22E)-(1R,3R)-1,3-Bis-(tert-butyldimethyl-silanyloxy)-23-[3-(1-methyl-1-trimethylsilanyloxy-ethyl)-phenyl]-19,24-dinor-9,10-seco-chola-5,7,22-triene from (E)-(1R,3aR,7aR)-7a-Methyl-1-[(R)-1-methyl-3-(1-Methyl-1-trimethylsilanyloxyethyl)phenyl]-allyl]-octahydro-inden-4-one.

MS: (M)$^+$ 765

IR: cm$^{-1}$ 2954; 2931; 2886; 2857; 1598; 1577; 1471; 1440; 1360; 1281; 1253; 1155; 1087; 1051; 1036; 1003; 963; 922; 836; 777; 692.

EXAMPLE 4A (7E,22E)-(1R,3R)-1,3-Bis-(tert-butyldimethyl-silanyloxy)-23-[3-(1-methyl-1-trimethylsilanyloxy-ethyl)-phenyl]-19,24-dinor-9,10-seco-chola-5,7,22-triene from (E)-(1R,3aR,7aR)-7a-Methyl-1-[(R)-1-methyl-3-[3-(1-methyl-1-trimethylsilanyloxy-ethyl)-phenyl]-allyl]-octahydro-inden-4-one.

MS: (M-tBu-Si—OH)$^+$ 632

IR: cm$^{-1}$ 2954; 2887; 2856; 1602; 1467; 1361; 1252; 1172; 1086; 1048; 963; 922; 903; 878; 837; 775; 701.

EXAMPLE 5A (7E)-(1R,3R)-1,3-Bis-(tert-butyldimethyl-silanyloxy)-23-[2-(1-methyl-1-trimethyl-silanyloxy-ethyl)-phenyl]-19,24-dinor-9,10-seco-chola-5,7-diene from [1R,3R,7aR)-7a-Methyl-1-[(S)-1-methyl-3-[2-(1-methyl-1-trimethylsilanyloxy-ethyl)-phenyl]-propenyl]-octahydro-inden-4-one.

MS: (M)$^+$ 767

IR: cm$^{-1}$ 2952; 2856; 1620; 1468; 1378; 1358; 1251; 1158; 1086; 1026; 837; 775; 752.

EXAMPLE 6A (7E)-(1R,3R)-1,3-Bis-(tert-butyldimethyl-silanyloxy)-23-[2-(1-methyl-1-trimethylsilanyloxy-ethyl)-phenyl]-19, 24-dinor-9,10-seco-chola-5,7-diene-22-yne from (1R,3aR,7aR)-7a-Methyl-1-[(S)-1-methyl-3-[2-(1-methyl-1-trimethylsilanyloxy-ethyl)-phenyl]-prop-2-ynyl]-octahydro-inden-4-one.

MS: (M)+ 762

IR: cm$^{-1}$ 2953; 2930; 2884; 2857; 1621; 1470; 1359; 1252; 1080; 1048; 836; 775; 758.

EXAMPLE 7A (7E)-(1R,3R)-1,3-Bis-(tert-butyldimethyl-silanyloxy)-23-[3-(1-methyl-1-trimethylsilanyloxy-ethyl)-phenyl]-19,24-dinor-9,10-seco-chola-5,7-diene from (1R,3aR,7aR)-7a-Methyl-1-[(R)-1-methyl-3-[3-(1-methyl-1-trimethylsilanyloxy-ethyl)-phenyl]-propenyl]-octahydro-inden-4-one.

MS: (M)$^+$ 767

IR: cm$^{-1}$ 2953; 2929; 2885; 2856; 1600; 1467; 1372; 1355; 1248; 1086; 1028; 837; 767.

EXAMPLE 8A (7E)-(1R,3R)-1,3-Bis-(tert-butyldimethyl-silanyloxy)-23-[3-(1-methyl-1-trimethylsilanyloxy-ethyl)-phenyl]-19,24-dinor-9,10-seco-chola-5,7-dien-22-yne from (1R, 3aR, 7aR)-7a-Methyl-1-[(S)-1-methyl-3-[3-(1-methyl-1-trimethyl-silanyloxy-ethyl)-phenyl]-prop-2-ynyl]-octahydro-inden-4-one.

MS: (M)$^+$ 763

IR: cm$^{-1}$ 2953; 2929; 2884; 2855; 1470; 1358; 1252; 1084; 1046; 835; 774; 696.

EXAMPLE 9A (7E)-(1R,3R)-1,3-Bis-(tert-butyldimethyl-silanyloxy)-23-[4-(1-methyl-1-trimethylsilanyloxy-ethyl)-phenyl]-19,24-dinor-9,10-seco-chola-5,7-diene from (1R,3aR, 7aR)-7a-Methyl-1-[(R)-1-methyl-3-[4-(1-methyl-1-trimethyl-silanyloxy-ethyl)-phenyl]-propyl]-octahydro-inden-4-one.

MS: (M)+ 767

IR: cm$^{-1}$ 2953; 2884; 2856; 1620; 1468; 1380; 1861; 1252; 1172; 1086; 1030; 917; 836; 775.

EXAMPLE 10A (7E)-(1R,3R)-1,3-Bis-(tert-butyldimethyl-silanyloxy)-23-[4-(1-methyl-1-trimethylsilanyloxy-ethyl)-phenyl]-19,24-dinor-9,10-seco-chola-5,7-dien-22-yne from (1R, 3aR, 7aR)-7a-Methyl-1-[(S)-1-methyl-3-[4-(1-methyl-1-trimethyl-silanyloxy-ethyl)-phenyl]-prop-2-ynyl]-octahydro-inden-4-one.

MS: (M)$^+$ 763

IR: cm$^{-1}$ 2954; 2931; 2885; 2857; 1620; 1502; 1467; 1377; 1359; 1253; 1173; 1091; 1046; 961; 916; 836; 775.

EXAMPLE 11A (7E)-(1R,3R)-1,3-Bis-(tert-butyldimethyl-silanyloxy)-23-[3-(tert-butyldimethyl-silanyloxy)-phenyl]-19,24-dinor-9,10-seco-chola-5,7-dien-22-yne from (1R,3aR,7aR)-7a-Methyl-1-[(R)-3-[4-(tert-butyldimethyl-silanyloxy)-1-methyl-phenyl]-propenyl]-octahydro-inden-4-one.

MS: (M–H)$^+$ 762

IR: cm$^{-1}$ 2954; 2930; 2885; 2857; 1596; 1574; 14751 1426; 1360; 1289; 1254; 1195; 1086; 1025; 939; 878; 837; 777; 687.

EXAMPLE 12A (7E)-(1R,3R)-1,3-Bis-(tert-butyldimethyl-silanyloxy)-23-[3-(tert-buty-ldimethyl-silanyloxy)-phenyl]-19,24-dinor-9,10-seco-chola-5,7-diene from (1R,3aR,7aR)-7a-Methyl-1-[(R)-3-[3-(tert-butyldimethyl-silanyloxy)-1-methyl-phenyl]-propyl]-octahydro-inden-4-one.

MS: (M)$^+$ 767

IR: cm$^{-1}$ 2952; 2930; 2885; 2857; 1604; 1583; 1468; 1441; 1376; 1360; 1253; 1156; 1086; 1050; 1026; 1004; 960; 922; 837; 777; 696; 664.

EXAMPLE 13A (7E)-(1R,3R)-1,3-Bis-(tert-butyldimethyl-silanyloxy)-23-[4-(tert-butyl-dimethyl-silanyloxy)-phenyl]-19,24-dinor-9,10-seco-chola-5,7-dien-22-yne from (1R,3aR,7aR)-1-[(S)-3-[4-(tert-Butyldimethyl-silanyloxy)-1-methyl-phenyl]-prodynyl]-7a-methyl-octahydro-inden-4-one.

MS: (M)$^+$763

IR: cm$^{-1}$ 2956; 2930; 2886; 2857; 1602; 1507; 1469; 1360; 1255; 1089; 1051; 1026; 915; 837; 805; 777.

EXAMPLE 14A (5Z,7E)-(1S,3R,20R)-1,3-Bis-(tert-butyldimethyl-silanyloxy)-23-[3-(1-methyl-1-trimethylsilanyloxy-ethyl)-phenyl]-24-nor-9,10-seco-chola-5,7,10(19)-trien-22-yne from (1R,3aR,7aR)-7a-Methyl-1-[(R)-1-methyl-3-[3-(1-methyl-1-trimethyl-silanyloxy-ethyl)-phenyl]-prop-2-ynyl]-octahydro-inden-4-one.

MS: (M)$^+$ 774.7

IR: cm$^{-1}$ 2954; 2930; 2885; 2857; 1652; 1602; 1468; 1377; 1361; 1317; 1253; 1223; 1177; 1084; 1043; 1006; 909; 885; 836; 775; 701.

EXAMPLE 15A (7E)-(1R,3R,20R)-1,3-Bis-(tert-butyldimethyl-silanyloxy)-23-[3-(1-methyl-1-trimethylsilanyloxy-ethyl)-phenyl]-19,24-dinor-9,10-seco-chola-5,7-dien-22-yne from (1R,3aR,7aR)-7a-Methyl-1-[(R)-1-methyl-3-[3-(1-methyl-1-trimethyl-silanyloxy-ethyl)-phenyl]-prop-2-ynyl]-octahydro-inden-4-one.

MS: (M)$^+$ 762.6

IR: cm$^{-1}$ 2953; 2929; 2885; 2856; 2241; 1625; 1602; 1468; 1378; 1360; 1252; 1221; 1176; 1086; 1048; 961; 902; 836; 800; 774; 699.

EXAMPLE 16A (5Z,7E)-(1S,3R,20R)-1,3-Bis-(tert-butyldimethyl-silanyloxy)-23-[2-(1-methyl-1-trimethylsilanyloxy-ethyl)-phenyl]-24-nor-9,10-seco-chola-5,7,10(19)-trien-22-yne from (1R,3aR,7aR)-7a-Methyl-1-[(R)-1-methyl-3-[2-(1-methyl-1-trimethyl-silanyloxy-ethyl)-phenyl]-prop-2-ynyl]-octahydro-inden-4-one.

MS: (M)$^{30}$ 774.5

IR: cm$^{-1}$ 2953; 2930; 2886; 2857;1645; 1470; 1440; 1376; 1360;1253; 1176; 1078; 1045; 1006; 909; 879; 835; 777; 702; 683.

EXAMPLE 17A (7E)-(1R,3R,20R)-1,3-Bis-(tert-butyldimethyl-silanyloxy)-23-[2-(1-methyl-1-trimethylsilanyloxy-ethyl)-phenyl]-19,24-dinor-9,10-seco-chola-5,7-dien-22-yne from (1R,3aR,7aR)-7a-Methyl-1-[(R)-1-methyl-3-[2-(1-methyl-1-trimethyl-silanyloxy-ethyl)-phenyl]-prop-2-ynyl]-octahydro-inden-4-one.

MS: (M)$^+$ 762.6

IR: cm$^{-1}$ 2954; 2930; 2857; 1620; 1470; 1359; 1252; 1175; 1085; 1048; 960; 908; 836; 776; 757; 698; 667.

EXAMPLE 18A (5Z,7E)-(1S,3R,20R)-1,3-Bis-(tert-butyldimethyl-silanyloxy)-23-[3-(1-methyl-1-trimethylsilanyloxy-ethyl)-phenyl]-24-nor-9,10-seco-chola-5,7,10(19)-triene from (1R,3aR,7aR)-7a-Methyl-1-[(S)-1-methyl-3-[3-(1-methyl-1-trimethyl-silanyloxy-ethyl)-phenyl]-propyl]-octahydro-inden-4-one.

MS: (M)+ 778.7

IR: cm−1 2954; 2930; 2884; 2856; 1645; 1603; 1468; 1459; 1377; 1360; 1252; 1175; 1085; 1043; 909; 875; 837; 775; 706.

EXAMPLE 19A (7E)-(1R,3R,20R)-1,3-Bis-(tert-butyldimethyl-silanyloxy)-23-[3-(1-methyl-1-trimethylsilanyloxy-ethyl)-phenyl]-19,24-dinor-9,10-seco-chola-5,7-diene from (1R,3aR, 7aR)-7a-Methyl-1-[(S)-1-methyl-3-[3-(1-methyl- I -trimethyl-silanyloxy-ethyl)-phenyl]-propyl]-octahydro-inden-4-one.

MS: (M)+ 766.7

IR: cm−1 2953; 2929; 2885; 2856;1602; 1468; 1462; 1379; 1358; 1252; 1177; 1087; 1048; 1030; 962; 922; 837; 775; 706.

EXAMPLE 20A (5Z,7E)-(1S,3R,20R)-1,3-Bis-(tert-butyldimethyl-silanyloxy)-23-[3-(tert-butyldimethyl-silanyloxy)-phenyl]-24-nor-9,10-seco-chola-5,7,10(19)-triene-22-yne from (1R,3aR,7aR)-7a-Methyl-1-[(R)-1-methyl-3-[3-(tert-butyl-dimethyl-silanyloxy)-phenyl]-prop-2-ynyl]-octahydro-inden-4-one.

MS: (M)+ 774.7

IR: cm−1 2954; 2930; 2885; 2857; 1596; 1574; 1475; 1424; 1360; 1288; 1254; 1198; 1087; 1050; 1027; 1004; 980; 960; 941; 904; 878; 836; 777; 687.

EXAMPLE 21A (7E)-(1R,3R,20R)-1,3-Bis-(tert-butyldimethyl-silanyloxy)-23-[3-(tert-butyldimethyl-silanyloxy)-phenyl]-19,24-dinor-9,10-seco-chola-5,7-diene -22-yne from (1R,3aR,7aR)-7a-Methyl-1-[(R)-1-methyl-3-[3-(tert-butyl-dimethyl-silanyloxy)-phenyl]-prop-2-ynyl]-octahydro-inden-4-one.

MS: (M)+ 762.6

IR: cm−1 2954; 2931; 2885; 2857; 1596; 1574; 1475; 1424; 1376; 1360; 1289; 1254; 1198; 1156; 1086; 1051; 1027; 1004; 981;961;942; 905; 878; 836; 778; 688; 664.

EXAMPLE 22A (5Z,7E,22E)-(1S,3R,20S)-1,3-Bis-(tert-butyldimethyl-silanyloxy)-23-[3-(tert-butyldimethyl-silanyloxy)-phenyl]-24-nor-9,10-seco-chola-5,7,10 (19),22-tetraene from E-(1R,3aR,7aR)-7a-Methyl-1-[(S)-1-methyl-3-[3-(tert-butyl-dimethyl-silanyloxy)-phenyl]-allyl]-octahydro-inden-4-one.

MS: (M)+ 776.5

IR: cm−1 2955; 2930; 2888; 2857; 1599; 1577; 1470; 1438; 1362; 1280; 1254; 1158; 1081; 989; 909; 835; 777; 687.

EXAMPLE 23A (7E,22E)-(1R,3R,20S)-1,3-Bis-(tert-butyldimethyl-silanyloxy)-23-[3-(tert-butyl-dimethyl-silanyloxy)-phenyl]-19,24-dinor-9,10-seco-chola-5,7,22-triene from E-(1R,3aR,7aR)-7a-Methyl-1-[(S)-1-methyl-3-[3-(tert-butyl-dimethyl-silanyloxy)-phenyl]-allyl]-octahydro-inden-4-one.

EXAMPLE 24A (7E)-(1R,3R)-1,3-Bis-(tert-butyl-dimethyl=silanyloxy)-23-[5-(1-(trimethyl-silanyloxy-1-methyl-ethyl)-furan-2-yl]-19,24-dinor-9,10-seco-chola-5,7-dien-22-yne from (1R,3R,7aR)-7a-Methyl-1-[(S)-1-methyl-3-[5-(1-methyl-1-trimethylsilanyloxy-ethyl)-furan-2-yl]-prop-2-ynyl]-octahydro-inden-4-one.

MS: (M)+ 753.7

IR: cm−1 2994; 2929; 2885; 2856; 1472; 1463; 1449; 1434; 1379; 1361; 1251; 1185; 1162; 1088; 1051; 1023; 1006;960; 899; 875; 837; 774.

EXAMPLE 25A (5Z,7E)-(1S,3S)-1,3-Bis-(tert-butyl-dimethyl-silanyloxy)-23-[5-(1-trimethyl-silanyloxy-1-methyl-ethyl)-furan-2-yl]-19-nor-9,10-seco-chola-5,7,10(24)-trien-22-yne from (1R,3R,7aR)-7a-Methyl-1-[(S)-1-methyl-3-[5-(1-methyl-1-trimethylsilanyloxy-ethyl)-furan-2-yl]-prop-2-ynyl]-octahydro-inden-4-one.

MS: (M)+ 764.7

EXAMPLE 26A (5Z,7E)-(3R),3-(tert-Butyl-dimethyl-silanyloxy)-23-[5-(1-trimethylsilanyloxy-1-methyl-ethyl)-furan-2-yl]-19-nor-9,10-seco-chola-5,7,10(19)-trien-22-yne-3-ol from (1R,3R,7aR)-7a-Methyl-1-[(S)-1-methyl-3-[5-(1-methyl-1-trimethylsilanyloxy-ethyl)-furan-2-yl]-prop-2-ynyl]-octahydro-inden-4-one.

MS: (M)+ 634.5

Typically, the product of formula III, (3R,5R)-[2-[3,5-bis-(tert-butyl-dimethyl-silanyloxy)-cyclohexylidene]-ethyl]-diphenyl-phosphine oxide Tetrahedron Lett. 1991, 32, 7666) (399 mg; 0.698 mmol) was dissolved in dry THF (3 ml). At −78° C. butyl lithium (1.6M in hexane; 0.530 ml; 0.848 mmol) was slowly added. The reaction mixture turned to an intense red color and was stirred for 30 minutes. Then the compound (E)-(1R,3R,7aR)-7a-Methyl-1-[(R)-1-methyl-3-[4-(1-methyl-1-trimethylsilanyloxy-ethyl)-phenyl]-prop-2-enyl]-octahydro-inden-4-one (144 mg; 0.349 mmol) was slowly added. After one hour at −78° C. the reaction mixture was allowed to reach slowly room temperature. The reaction mixture was then poured on chilled brine, extracted twice with ether, washed twice with brine, dried over anhydrous sodium sulfate and the solvents were removed. After flash-chromatography (eluent: hexanes/ethyl-acetate 95/5) the compound of formula II of the above Example 1A, (7E, 22E)-(1R,3R)-1,3-Bis-(tert-butyldimethyl-silanyloxy)-23-[4-(1-methyl-1-trimethylsilanyloxy-ethyl)-phenyl]-19,24-dinor-9,10-seco-chola-5,7,22-triene (228 mg; 85% yield) was obtained as a colorless foam.

For preparing compounds II containing a methylene group in the A-ring, (3S,5R)-[2-[3,5-bis-(tert-butyl-dimethyl-silanyloxy)-2-methylene-cyclohexylidene]-ethyl]-diphenyl-phosphine oxide was used instead of the above used phosphine oxide.

B) The following compounds of formula IV were obtained from compounds of formula V:

EXAMPLE 1B (E)-(1R,3R,7aR)-7a-Methyl-1-[(R)-1-methyl-3-[4-(1-methyl-1-trimethyl-silanyl-oxy-ethyl)-phenyl]-prop-2- enyl]-octahydro-inden-4-one from (E)-(1R,3aR,4S,7aR)-1-[(R)-1-Methyl-3-[4-(1-hydroxy-1-methyl-ethyl)-phenyl-propenyl]-7a-methyl-octahydro-inden-4-ol.

MS: (M)⁺ 412

IR: cm⁻¹ 2959; 2874; 1714; 1507; 1458; 1379; 1254; 1173; 1098; 1039; 969; 912; 840; 755.

EXAMPLE 2B (E)-(1R,3R,7aR)-7a-Methyl-1-[(R)-1-methyl-3-[2-(1-methyl-1-trimethyl-silanyloxy-ethyl)-phenyl]-allyl]-octahydro-inden-4-one from (E)-(1R,3aR,4S,7aR)-1-[(R)-1-Methyl-3-[2-(1-hydroxy-1-methyl-ethyl)-phenyl-propenyl]-7a-methyl-octahydro-inden-4-ol.

MS: (M)⁺ 412

IR: cm⁻¹ 2958; 2873; 1714; 1457; 1380; 1248; 1158; 1025; 913; 838; 757.

EXAMPLE 3B (E)-(1R,3R,7aR)-7a-Methyl-1-[(R)-1-methyl-3-[3-(1-methyl-1-trimethyl-silanyloxy-ethyl)-phenyl]-allyl]-octahydro-inden-4-one from (E)-(1R,3aR,4S,7aR)-1-[(R)-3-[3-(1-hydroxy-1-methyl-ethyl)-phenyl-propeny]-7a-methyl-octahydro-inden-4-ol.

MS: (M)⁺ 412

IR: cm⁻¹ 2959; 2874; 1714; 1500; 1458; 1379; 1251; 1175; 1085; 1039; 968; 878; 841; 790; 754; 703.

EXAMPLE 4B

[1R,3R,7aR)-7a-Methyl-1-[(S)-1-methyl-3-[2-(1-methyl-1-trimethyl-silanyloxy-ethyl)- phenyl]-propenyl]-octahydro-inden-4-one from [1R,3aR,4S,7aR]-7a-Methyl-1-[(S)-1-methyl-3-[2-(1-hydroxy-1-methyl-ethyl)-phenyl-propenyl]-octahydro-inden-4-ol.

MS: (M−CH₃)⁺ 399

IR: cm⁻¹ 2958; 2875; 1715; 1465; 1445; 1380; 1248; 1159; 1026; 912; 839; 757.

EXAMPLE 5B (1R,3aR,7aR)-7a-Methyl-1-[(S)-1-methyl-3-[2-(1-methyl-1-trimethylsilanyl-oxy-ethyl)-phenyl]-prop-2-ynyl]-octahydro-inden-4-one from [1R,3aR,4S,7aR]-7a-Methyl-1-[(R)-1-methyl-3-[2-(1-hydroxy-1-methyl-ethyl)-phenyl-propynyl]-octahydro-inden-4-ol.

MS: (M)⁺ 410

IR: cm⁻¹ 2964; 2876; 1715; 1476; 1455; 1379; 1249; 1176; 1073; 1044; 910; 841; 759.

EXAMPLE 6B (1R,3aR,7aR)-7a-Methyl-1-[(R)-1-methyl-3-[3-(1-methyl-1-trimethylsilanyl-oxy-ethyl)-phenyl]-propenyl]-octahydro-inden-4-one from [1R,3aR,4S,7aR]-7a-Methyl-1-[(S)-1-methyl-3-[3-(1-hydroxy-1-methyl-ethyl)-phenyl-propenyl]-octahydro-inden-4-ol.

MS: (M+H)⁺ 415

IR: cm⁻¹ 2958; 2874; 1715; 1607; 1458; 1380; 1251; 1175; 1088; 1037; 840; 796; 755; 707.

EXAMPLE 7B (1R,3aR,7aR)-7a-Methyl-1-[(S)-1-methyl-3-[3-(1-methyl-1-trimethylsilanyl-oxy-ethyl)-phenyl]-prop-2-ynyl]-octahydro-inden-4-one from [1R,3aR,4S,7aR]-7a-Methyl-1-[(R)-1-methyl-3-[3-(1-hydroxy-1-methyl-ethyl)-phenyl-propynyl]-octahydro-inden-4-ol.

MS: (M)⁺ 410

IR: cm⁻¹ 2963; 2876; 1715; 1598; 1470; 1455; 1380; 1307; 1250; 1176; 1083; 1040; 904; 841; 796; 755; 701.

EXAMPLE 8B (1R,3aR,7aR)-7a-Methyl-1-[(R)-1-methyl-3-[4-(1-methyl-1-trimethylsilanyl-oxy-ethyl)-phenyl]-propenyl]-octahydro-inden-4-one from [1R,3aR,4S,7aR]-7a-Methyl-1-[(S)-1-methyl-3-[4-(1-hydroxy-1-methyl-ethyl)-phenyl-propenyl]-octahydro-inden-4-ol.

MS: (M−CH₃)⁺ 399

IR: cm⁻¹ 2958; 2874; 1715; 1512; 1458; 1379; 1252; 1173; 1101; 1037; 913; 840; 757.

EXAMPLE 9B (1R,3aR,7aR)-7a-Methyl-1-[(S)-1-methyl-3-[4-(1-methyl-1-trimethylsilanyl-oxy-ethyl)-phenyl]-prop-2-ynyl]-octahydro-inden-4-one from [1R,3aR,4S,7aR]-7a-Methyl-1-[(R)-1-methyl-3-[4-(1-hydroxy-1-methyl-ethyl)-phenyl-propynyl]-octahydro-inden-4-ol.

MS: (M)⁺ 410

IR: cm⁻¹ 2963; 2876; 1715; 1502; 1455; 1380; 1253; 1174; 1096; 912; 839; 755.

EXAMPLE 10B (1R,3aR,7aR)-7a-Methyl-1-[(R)-1-methyl-3-[3-(1-methyl-1-trimethylsilanyl-oxy-ethyl)-phenyl]-prop-2-ynyl]-octahydro-inden-4-one from [1R,3aR,4S,7aR]-7a-Methyl-1-[(R)-3-[3-(1-hydroxy-1-methyl-ethyl)-phenyl]-1-methyl-prop-2-ynyl]-octahydro-inden-4-ol.

MS: (M)⁺ 410

IR: cm⁻¹ 2964; 2875; 1714; 1600; 1480; 1455; 1415; 1381; 1315; 1250; 1225; 1176; 1084; 1039; 841; 799; 756; 701.

EXAMPLE 11B (1R,3aR,7aR)-7a-Methyl-1-[(R)-1-methyl-3-[2-(1-methyl-1-trimethylsilanyl-oxy-ethyl)-phenyl]-prop-2-ynyl]-octahydro-inden-4-one from [1R,3aR,4S,7aR]-7a-Methyl-1-[(R)-3-[2-(1-hydroxy-1-methyl-ethyl)-phenyl]-1-methyl-prop-2-ynyl]-octahydro-inden-4-ol.

MS: (M)⁺ 410

IR: cm⁻¹ 2964; 2875; 1715; 1476; 1455; 1379; 1313; 1248; 1175; 1071; 1045; 909; 842; 759.

EXAMPLE 12B (1R,3aR,7aR)-7a-Methyl-1-[(S)-1-methyl-3-[3-(1-methyl-1-trimethylsilanyl-oxy-ethyl)-phenyl]-propyl]-octahydro-inden-4-one from [1R,3aR,4S,7aR]-7a-Methyl-1-[(S)-3-[3-(1-hydroxy-1-methyl-ethyl)-phenyl]-1-methyl-propyl]-octahydro-inden-4-ol.

MS: (M+H)⁺ 415

IR: cm⁻¹ 2960; 2875; 1715; 1462; 1383; 1250; 1175; 1096; 1038; 840; 800; 762; 712.

EXAMPLE 13B (1R,3R,7aR)-7a-Methyl-1-[(S)-1-methyl-3-[5-(1-methyl-1-trimethylsilanyloxy-ethyl)-furan-2-yl]-prop-2-ynyl]-octahydro-inden-4-one from [1R,3aR,4S,7aR]-7a-Methyl-1-[(R)-1-methyl-3-[5-(1-methyl-1-hydroxy-ethyl)-furan-2-yl]-prop-2-ynyl]-octahydro-inden-4-ol.

MS: (M)⁺ 400

IR: cm$^{-1}$ 2963; 2876; 1716; 1542; 1455; 1380; 1364; 1262; 1251; 1217; 1206; 1184; 1162; 1123; 1036; 898; 842; 791; 756.

Typically, the compound of formula V, (E)-(1R,3aR,4S,7aR)-1-[(R)-1-Methyl-3-[4-(1-hydroxy-1-methyl-ethyl)-phenyl-propenyl]-7a-methyl-octahydro-inden-4-ol (137 mg; 0.40 mmol) was dissolved in DMF (6 ml). PDC (226 mg; 0.60 mmol) was added portion wise at room temperature, and the stiring was resumed for one hour. The reaction mixture was then poured on chilled brine, extracted twice with ethyl acetate, washed twice with brine, dried over anhydrous sodium sulfate and the solvent was removed. After flash-chromatography (eluent: hexanes/ethyl-acetate 67/33), the obtained intermediate was dissolved in dry THF (6 ml). Then, at 0° C. 1-trimethylsilyl-imidazol (57.7 ml; 0.394 mmol), imidazol (13.4 mg; 0.197 mmol) and trimethylsilylchloride (24.9 ml; 0.197 mmol) were added sequentially. After twenty minutes at –0° C. the reaction mixture was allowed to reach slowly room temperature. The reaction mixture was then poured on chilled brine, extracted twice with ethyl acetate, washed twice with brine, dried over anhydrous sodium sulfate and the solvents were removed. After flash-chromatography (eluent: hexanes/ethyl-acetate 85/15) the compound of formula IV in the above Example 1B, (E)-(1R,3R,7aR)-7a-Methyl-1-[(R)-1-methyl-3-[4-(1-methyl-1-trimethyl-silanyl-oxy-ethyl)-phenyl]-prop-2-enyl]-octahydro-inden-4-one (148 mg; 89% yield) was obtained as a yellow oil.

C) The following compounds of formula IV were obtained from compounds of formula V:

EXAMPLE 1C (E)-(1R,3R,7aR)-7a-Methyl-1-[(R)-1-methyl-3-[3-(tert-butyldimethylsilanyl-oxy)-phenyl]-allyl]-octahydro-inden-4-one from (E)-(1R,3aR,4S,7aR)-1-[(R)-1-Methyl-3-[3-(hydroxy-phenyl)-propenyl]-7a-methyl-octahydro-inden-4-ol.

MS: (M)$^+$ 412

IR: cm$^{-1}$ 2956; 2931; 2888; 2861; 1708; 1599; 1577; 1485; 1465; 1429; 1382; 1282; 156; 1160; 978; 859; 782; 692.

EXAMPLE 2C (1R,3aR,7aR)-1-[(S)-1-Methyl-3-[3-(tert-butyl-dimethyl-silanyloxy)-phenyl]prop-2-ynyl]-7a-methyl-octahydro-inden-4-one from [1R,3aR,4S,7aR]-1-[(S)-1-methyl-3-(3-hydroxy-phenyl)-prop-2-ynyl]-7a-methyl octahydro-inden-4-ol.

EXAMPLE 3C (1R,3aR,7aR)-1-[(R)-1-methyl-3-[3-(tert-Butyldimethyl-silanyloxy)-phenyl]-prop-2-ynyl]-7a-methyl-octahydro-inden-4-one (from (1R,3aR,4S,7aR)-1-[(R)-1-methyl-3-(3-hydroxy-phenyl)-prop-2-ynyl]-7a-methyl-octahydro-inden-4-ol.

MS: (M)$^+$ 414

IR: cm$^{-1}$ 2957; 2858; 1714; 1603; 1583; 1483; 1442; 1379; 1273; 1260; 1157; 976; 889; 842; 782; 696.

EXAMPLE 4C (1R,3aR,7aR)-1-[(S)-1-methyl-3-[4-(tert-Butyl-dimethyl-silanyloxy)-phenyl]-prop-2-ynyl]-7a-methyl-octahydro-inden-4-one from (1R,3aR,4S,7aR)-1-[(S)-3-[4-(tert-butyl-dimethyl-silanyloxy)-phenyl]-1-methyl-prop-2-ynyl]-7a-methyl-octahydro-inden-4-ol.

MS: (M)$^+$ 410

IR: cm$^{-1}$ 2958; 2932; 2882; 2858; 1715; 1602; 1506; 1469; 1380; 1262; 1166; 1096; 911; 841; 805; 781.

EXAMPLE 5C (1R,3aR,7aR)-7a-Methyl-1-[(R)-1-methyl-3-[3-(tert-butyl-dimethyl-silanyl-oxy)-phenyl]-prop-2-ynyl]-octahydro-inden-4-one from (1R,3aR,4S 7aR)-1-[(R)-1-Methyl-3-(3-hydroxy-phenyl)]-prop-2-ynyl]-7a-methyl octahydro-inden-4-ol.

MS: (M)$^+$ 410

IR: cm$^{-1}$ 2957; 2932; 2883; 2859; 2215; 1715; 1596; 1573; 1477; 1422; 1380; 1289; 1256; 1196; 1004; 976; 945; 913; 877; 839; 785; 689.

EXAMPLE 6C

E-(1R,3aR,7aR)-7a-Methyl-1-[(S)-1-methyl-3-[3-(tert-butyl-dimethylsilanyl-oxy)-phenyl]-allyl]-octahydro-inden-4-one from E-(1R,3aR,4S,7aR)-1-[(S)-1-methyl-3-[3-(tert-butyl-dimethyl-silanyloxy)-phenyl]-allyl]-7a-methyl-octahydro-inden-4-ol.

MS: (M)$^+$ 412

IR: cm$^{-1}$ 2958; 2859; 1714; 1598; 1576; 1477; 1380; 1280; 1254; 1156; 973; 853; 842; 783; 691.

Typically, the alcohol of formula V, (1R,3aR,4S,7aR)-1-[(R)-1-methyl-3-(3-hydroxy-phenyl)-prop-2-ynyl]-7a-methyl-octahydro-inden-4-ol(236 mg; 0.78 mmol) was dissolved in DMF (5 ml). Tert-butyldimethylsilylchloride (130 mg; 0.86 mmol) and imidazol (133 mg; 1.95 mmol) were added at room temperature, and the stirring was resumed for 24 hours. The reaction mixture was then poured on chilled aqueous HCl solution, extracted twice with ethyl acetate, washed twice with brine, dried over anhydrous sodium sulfate and the solvent was removed. After flash-chromatography (eluent: hexanes/ethyl-acetate 85/15), the intermediate (ketone of formula IV-A) was obtained as a yellow oil. The intermediate was dissolved in DMF (6 ml). PDC (333 mg; 0.885 mmol) was added portion wise at room temperature, and the stirring was resumed for one hour. The reaction mixture was then poured on chilled brine, extracted twice with ethyl acetate, washed twice with brine, dried over anhydrous sodium sulfate and the solvent was removed. After flash-chromatography (eluent: hexanes/ethyl-acetate 88/12) the compound of formula IV in the above Example 3C (1R,3aR,7aR)-7a-Methyl-1-[(R)-3-[3-(tert-butyldimethyl-silanyloxy)-1-methyl-phenyl]-prop-2-ynyl]-octahydro-inden-4-one (236 mg; overall yield: 73%) was obtained as a colorless oil.

D) The following compounds of formula V were obtained from compounds of formula VI:

EXAMPLE 1D (E)-(1R,3aR,4S,7aR)-1-[(R)-1-Methyl-3-[4-(1-hydroxy-1-methyl-ethyl)-phenyl-propenyl]-7a-methyl-octahydro-inden-4-ol from (E)-4-[(R)-3-[(1R,3aR,4S,7aR)-4-Hydroxy-7a-methyl-octahydro-inden-1-yl]-but-1-enyl]-benzoic acid ethyl ester.

MS: (M)$^+$ 342

IR: cm$^{-1}$ 3413; 2931; 2867; 1640; 1510; 1458; 1368; 1257; 1161; 1093; 961; 862; 814; 565.

EXAMPLE 2D (E)-(1R,3aR,4S,7aR)-1-[(R)-1-Methyl-3-[2-(1-hydroxy-1-methyl-ethyl)-phenyl-propenyl]-7a-methyl-octahydroinden-4-ol from (E)-2-[(R)-3-[(1R,3aR,4S,7aR)-4-Hydroxy-7a-methyl-octahydro-inden-1-yl]-but-1-enyl]-benzoic acid ethyl ester.

MS: (M)+ 342

IR: cm−1 3426; 2934; 2867; 1640; 1448; 1368; 1245; 1163; 1067; 989; 945; 761; 751.

EXAMPLE 3D (E)-(1R,3aR,4S,7aR)-1-[(R)-3-[3-(1-hydroxy-1-methyl-ethyl)-phenyl-propenyl]-7a-methyl-octahydro-inden-4-ol from (E)-3-[(R)-3-[(1R,3aR,4S,7aR)-4-Hydroxy-7a-methyl-octahydro-inden-1-yl]-but-1-enyl]-benzoic acid ethyl ester.

MS: (M)+ 342

IR: cm−1 3406; 2933; 2868; 1600; 1455; 1370; 1252; 1164; 963; 790; 700.

EXAMPLE 4D

[1R,3aR,4S,7aR]-7a-Methyl-1-[(S)-1-methyl-3-[2-(1-hydroxy-1-methyl-ethyl)-phenyl-propenyl]-octahydro-inden-4-ol [1R,3aR,4S,7aR]-7a-Methyl-1-[(S)-1-methyl-3-[2-(carboxylic acid ethyl ester)-phenyl-propenyl]-octahydro-inden-4-ol.

MS: (M−H$_2$O)+ 326

IR: cm−1 3405; 2936; 2870; 1468; 1442; 1373; 1241; 1065; 992; 943; 759.

EXAMPLE 5D

[1R,3aR,4S,7aR]-7a-Methyl-1-[(R)-1-methyl-3-[2-(1-hydroxy-1-methyl-ethyl)-phenyl-propynyl]-octahydro-inden-4-ol from (1R,3aR,4S,7aR)-4-Hydroxy-1-[(S)-3-[2-(carboxylic acid ethyl ester)-phenyl-1-methyl-propynyl]-7a-methyl-octahydro-indene.

MS: (M)+ 340

IR: cm−1 3422; 2919; 2850; 2213; 1470; 1429; 1398; 1340; 1283; 1219; 1122; 1095; 1059; 1031; 948; 721.

EXAMPLE 6D

[1R,3aR,4S,7aR]-7a-Methyl-1-[(S)-1-methyl-3-[3-(1-hydroxy-1-methyl-ethyl)-phenyl-propenyl]-octahydro-inden-4-ol from [1R,3aR,4S,7aR]-7a-Methyl-1-[(S)-1-methyl-3-[3-(carboxylic acid ethyl ester)-phenyl-propenyl]-octahydro-inden-4-ol.

MS: (M)+ 344

IR: cm−1 3398; 2930; 2868; 1604; 1487; 1441; 1371; 1263; 1163; 1068; 990; 952; 940; 886; 790; 706.

EXAMPLE 7D

[1R,3aR,4S,7aR]-7a-Methyl-1-[(R)-1-methyl-3-[3-(1-hydroxy-1-methyl-ethyl)-phenyl-propynyl]-octahydro-inden-4-ol from (1R,3aR,4S,7aR)-4-Hydroxy-1-[(S)-3-[3-(carboxylic acid ethyl ester)-phenyl-1-methyl-propynyl]-7a-methyl-octahydro-indene.

MS: (M)+ 340

IR: cm−1 3424; 2970; 2934; 2872; 2218; 1600; 1470; 1455; 1372; 1268; 1167; 992; 951; 894; 862; 796; 701.

EXAMPLE 8D

[1R,3aR,4S,7aR]-7a-Methyl-1-[(S)-1-methyl-3-[4-(1-hydroxy-1-methyl-ethyl)-phenyl-propenyl]-octahydro-inden-4-ol from [1R,3aR,4S,7aR]-7a-Methyl-1-[(S)-1-methyl-3-[4-(carboxylic acid ethyl ester)-phenyl-propenyl]-octahydro-inden-4-ol.

MS: (M)$^{30}$ 344

IR: cm−1 3377; 2974; 2938; 2867; 1510; 1459; 1407; 1376; 1316; 1261; 1165; 1141; 1098; 1078; 994; 952; 861; 810.

EXAMPLE 9D

[1R,3aR,4S,7aR]-7a-Methyl-1-[(R)-1-methyl-3-[4-(1-hydroxy-1-methyl-ethyl)-phenyl-propynyl]-octahydro-inden-4-ol from (1R,3aR,4S,7aR)-4-Hydroxy-1-[(S)-3-[4-(carboxylic acid ethyl ester)-phenyl-1-methyl-propynyl]-7a-methyl-octahydro-indene.

MS: (M)+ 340

IR: cm−1 3412; 2970; 2932; 2870; 2214; 1602; 1502; 1455; 1365; 1257; 1167; 1107; 1042; 988; 950; 857; 835; 569.

EXAMPLE 10D

[1R,3aR,4S,7aR]-7a-Methyl-1-[(S)-3-[3-(1-hydroxy-1-methyl-ethyl)-phenyl]-1-methyl-propyl]-octahydro-inden-4-ol from 3-[(S)-3-[(1R,3aR,4S,7aR)-4-Hydroxy-7a-methyl-octahydro-inden-1-yl]-butyl]-benzoic acid ethyl ester.

MS: (M)+ 344

IR: cm−1 3406; 2932; 2869; 1726; 1608; 1490; 1457; 1374; 1261; 1166; 1087; 989; 951; 890; 837; 792; 707.

EXAMPLE 11D

[1R,3aR,4S,7aR]-7a-Methyl-1-[(R)-3-[3-(1-hydroxy-1-methyl-ethyl)-phenyl]-1-methyl-prop-2-ynyl]-octahydro-inden-4-ol from (1R,3aR,4S,7aR)-4-Hydroxy-1-[(R)-3-[3-(carboxylic acid ethyl ester)-phenyl-1-methyl-propynyl]-7a-methyl-octahydro-indene.

MS: (M)+ 340

IR: cm−1 3397; 2969; 2933; 2870; 2230; 1600; 1480; 1454; 1415; 1370; 1310; 1268; 1082; 1068; 987; 952; 892; 862; 794; 708.

EXAMPLE 12D

[1R,3aR,4S,7aR]-7a-Methyl-1-[(R)-3-[2-(1-hydroxy-1-methyl-ethyl)-phenyl]-1-methyl-prop-2-ynyl]-octahydro-inden-4-ol from (1R,3aR,4S,7aR)-4-Hydroxy-1-[(R)-3-[2-(carboxylic acid ethyl ester)-phenyl-1-methyl-propynyl]-7a-methyl-octahydro-indene.

MS: (M)+ 340

IR: cm−1 3439; 2931; 2869; 2220; 1477; 1450; 1438; 1366; 1307; 1265; 1231; 1166; 1119; 1065; 1034; 988; 949; 855; 759.

EXAMPLE 13D

[1R,3aR,4S,7aR]-7a-Methyl-1-[(R)-1-methyl-3-[5-(1-methyl-1-hydroxy-ethyl)-furan-2-yl]-prop-2-ynyl]-octahydro-inden-4-ol from [1R,3aR,4S,7aR]-7a-Methyl-4-butyl-dimethyl-silanyloxy)-1-[(R)-1-methyl-3-[5-carboxylic acid ethyl ester-furan-2-yl]-prop-2-ynyl]-octahydro-indene.

MS: (M)+ 330

IR: cm−1 3409; 2969; 2934; 2872; 1732; 1719; 1504; 1455; 1373; 1305; 1256; 1201; 1166; 1145; 1120; 1021; 963; 946; 789.

Typically, the compound of formula VI (E)-4-[(R)-3-[(1R,3aR,4S,7aR)4-hydroxy-7a-methyl-octahydro-inden-1-yl]-but-1-enyl]-benzoic acid ethyl ester (177 mg; 0.496 mmol) was dissolved in dry THF (6 ml). Methylmagnesiumchlorid (3M solution in THF; 1.0 ml; 2.98 mmol) was added at 0° C. And the reaction was stirred for three hours at room temperature. The reaction mixture was then poured on chilled brine, extracted twice with ethyl acetate, washed twice with brine, dried over anhydrous sodium sulfate and the solvent was removed. After flash-chromatography (eluent: hexanes/ethyl-acetate 67/33) the compound of formula V of the above Example ID (E)-(1R,3aR,4S,7aR)-1-[(R)-1-Methyl-3-[4-(1-hydroxy-1-methyl-ethyl)-phenyl-propenyl]-7a-methyl-octahydro-inden-4-ol (144 mg; yield: 85%) was obtained as a colorless foam.

E) The following compounds of formula VI were obtained by hydrogenation in the side chain:

EXAMPLE 1E

[1R,3aR,4S,7aR]-7a-Methyl-1-[(S)-1-methyl-3-[2-(carboxylic acid ethyl ester)-phenyl-propenyl]-octahydro-inden-4-ol from (1R,3aR,4S,7aR)-4-Hydroxy-1-[(S)-3-[2-(carboxylic acid ethyl ester)-phenyl-1-methyl-propynyl]-7a-methyl-octahydro-indene.

MS: (M)+ 358

IR: cm−1 3500; 1720; 1602; 1577; 1447; 1368; 1257; 1167; 1136; 1098; 1069; 990; 942; 750; 711.

EXAMPLE 2E

[1R,3aR,4S,7aR]-7a-Methyl-1-[(S)-1-methyl-3-[3-(carboxylic acid ethyl ester)-phenyl-propenyl]-octahydro-inden-4-ol from (1R,3aR,4S,7aR)-4-Hydroxy-1-[(S)-3-[3 (carboxylic acid ethyl ester)-phenyl-1-methyl-propynyl]-7a-methyl-octahydro-indene.

MS: (M)+ 358

IR: cm−1 3528; 2939; 2868; 1719; 1608; 1590; 1444; 1369; 1280; 1197; 1104; 1024; 992; 946; 862; 751; 698.

EXAMPLE 3E

[1R,3aR,4S,7aR]-7a-Methyl-1-[(S)-1-methyl-3-[4-(carboxylic acid ethyl ester)-phenyl-propenyl]-octahydro-inden-4-ol from (1R,3aR,4S,7aR)-4-Hydroxy-1-[(S)-3-[4-(carboxylic acid ethyl ester)-phenyl-1-methyl-propynyl]-7a-methyl-octahydro-indene.

MS: (M)+ 358

IR: cm−1 1 3538; 2935; 2868; 1718; 1611; 1463; 1368; 1276; 1177; 1106; 1022; 993; 943; 850; 768; 708.

EXAMPLE 4E

3-[(S)-3-[(1R,3aR,4S,7aR)-4-Hydroxy-7a-methyl-octahydro-inden-1-yl]-butyl]-benzoic acid ethyl ester from (1R,3aR,4S,7aR)-4-Hydroxy-1-[(R)-3-[3-(carboxylic acid ethyl ester)-phenyl-1-methyl-propynyl]-7a-methyl-octahydro-indene.

MS: (M)+ 358

IR: cm−1 3528; 2932; 2870; 1719; 1609; 1591; 1445; 1370; 1282; 1197; 1105; 1024; 990; 947; 751; 695.

EXAMPLE 5E

3-[(R)-3-[(1R,3aR,4S,7aR)-4-Hydroxy-7a-methyl-octahydro-inden-1-yl]-butyl]-phenol from [1R,3aR,4S,7aR]-7a-Methyl-1-[(S)-1-methyl-3-(3-hydroxy-phenyl)-propynyl]-octahydro-inden-4-ol.

MS: (M)+ 302

IR: cm−1 3523; 3234; 3034; 2996; 2936; 2867; 1619; 1585; 1480; 1372; 1349; 1295; 1249; 1153; 1063; 982; 956; 941; 784; 695.

Typically, the compound of formula VI, (1R,3aR,4S,7aR)-4-Hydroxy-1-[(S)-3-[2-(carboxylic acid ethyl ester)-phenyl-1-methyl-propynyl]-7a-methyl-octahydro-indene (218 mg; 0.615 mmol) was dissolved in dry ethanol (12 ml). Palladium on carbon (10%; 55 mg) was added and the reaction was put under hydrogen at one atmosphere for 12 hours at room temperature. The catalyst was filtered off and the solvent was evaporated. The compound of formula VI of the above Example 1E, the [1R,3aR,4S,7aR]-7a-Methyl-1-[(S)-1-methyl-3-[2-(carboxylic acid ethyl ester)-phenyl-propenyl]-octahydro-inden-4-ol (226 mg; yield: 100%) was obtained as a yellowish oil.

F) The following compounds of formula V or VI were obtained from compounds of formula VII or IX

EXAMPLE 1F (1R,3aR,4S,7aR)-4-Hydroxy-1-[(S)-3-[2-(carboxylic acid ethyl ester)-phenyl-1-methyl-propynyl]-7a-methyl-octahydro-indene from (1R,3aR,4S,7aR)-4-(tert-Butyl-dimethyl-silanyloxy)-7a-methyl-1-[(S)-1-methyl-propynyl]-octahydro-indene.

MS: (M)+ 354

IR: cm−1 3530; 3440; 2934; 2872; 2218; 1726; 1597; 1568; 1481; 1446; 1367; 1292; 1248; 1165; 1131; 1080; 1042; 758.

EXAMPLE 2F (1R,3aR,4S,7aR)-4-Hydroxy-1-[(S)-3-[3-(carboxylic acid ethyl ester)-phenyl-1-methyl-propynyl]-7a-methyl-octahydro-indene from (1R,3aR,4S,7aR)-4-(tert-Butyl-dimethyl-silanyloxy)-7a-methyl-1-[(S)-1-methyl-propynyl]-octahydro-indene.

MS: (M)+ 354

IR: cm−1 3531; 2934; 2872; 2216; 1721; 1600; 1578; 1451; 1369; 1290; 1228; 1166; 1105; 1079; 1024; 992; 756; 685.

EXAMPLE 3F (1R,3aR,4S,7aR)-4-Hydroxy-1-[(S)-3-[4-(carboxylic acid ethyl ester)-phenyl-1-methyl-propynyl]-7a-methyl-octahydro-indene from (1R,3aR,4S,7aR)-4-(tert-Butyl-dimethyl-silanyloxy)-7a-methyl-1-[(S)-1-methyl-propynyl]-octahydro-indene.

MS: (M)+ 354

IR: cm−1 3530; 2934; 2872; 2216; 1719; 1605; 1451; 1405; 1368; 1272; 1174; 1106; 1022; 857; 770; 698.

EXAMPLE 4F

[1R,3aR,4S,7aR]-7a-Methyl-1-[(S)-1-methyl-3-(3-hydroxy-phenyl)-propynyl]-octahydro-inden-4-ol from [1R,3aR,4S,7aR]-7a-Methyl-1-[(S)-1-methyl-prop-2-ynyl]-octahydro-inden-4-ol.

MS: (M−H)+ 297

IR: cm−1 3441; 3140; 2946; 2881; 2220; 1611; 1571; 1479; 1450; 1359; 1327; 1285; 1182; 1157; 1064; 988; 947; 878; 783; 689.

EXAMPLE 5F (1R,3aR,4S,7aR)-1-[(S)-1-methyl-3-[4-(tert-Butyl-dimethyl-silanyloxy)-phenyl]-prop-2-ynyl]-7a-methyl-octahydro-inden-4-ol from [1R,3aR,4S,7aR]-7a-Methyl-1-[(S)-1-methyl-prop-2-ynyl]-octahydro-inden-4-ol.

MS: (M−H)+ 412

EXAMPLE 6F

[1R,3aR,4S,7aR]-7a-Methyl-1-[(R)-3-(3-hydroxy-phenyl)-1-methyl-prop-2-ynyl]-octahydro-inden-4-ol from [1R,3aR,4S,7aR]-7a-Methyl-1-[(R)-1-methyl-prop-2-ynyl]-octahydro-inden-4-ol.

MS: (M−H)+ 298

IR: cm$^{-1}$ 3561; 3226; 2938; 2875; 2228; 1611; 1570; 1471; 1453; 1377; 1328; 1291; 1234; 1183; 1153; 1085; 1000; 989; 958; 936; 888; 880; 789; 692.

EXAMPLE 7F (1R,3aR,4S,7aR)-4-Hydroxy-1-[(R)-3-[3-(carboxylic acid ethyl ester)-phenyl-1-methyl-prop-2-ynyl]-7a-methyl-octahydro-indene from (1R,3aR,4S,7aR)-4-(tert-Butyl-dimethyl-silanyloxy)-7a-methyl-1-[(R)-1-methyl-prop-2-ynyl]-octahydro-indene.

MS: (M−H)+ 354

IR: cm$^{-1}$ 3524; 3468; 2934; 2870; 2238; 1721; 1602; 1582; 1476; 1453; 1428; 1370; 1291; 1229; 1167; 1106; 1080; 1025; 989; 960; 756; 685.

EXAMPLE 8F (1R,3aR,4S,7aR)-4-Hydroxy-1-[(R)-3-[2-(carboxylic acid ethyl ester)-phenyl-1-methyl-prop-2-ynyl]-7a-methyl-octahydro-indene from (1R,3aR,4S,7aR)-4-(tert-Butyl-dimethyl-silanyloxy)-7a-methyl-1-[(R)-1-methyl-prop-2-ynyl]-octahydro-indene.

MS: (M−H)+ 354

IR: cm$^{-1}$ 3538; 3468; 2933; 2870; 2240; 1714; 1600; 1570; 1482; 1447; 1369; 1292; 1249; 1167; 1132; 1076; 1042; 989; 949; 758; 701.

EXAMPLE 9F

[1R,3aR,4S,7aR]-7a-Methyl-4-(tert-butyl-dimethyl-silanyloxy)-1-[(R)-1-methyl-3-[5-carboxylic acid ethyl ester-furan-2-yl]-prop-2-ynyl]-octahydro-indene from (1R,3aR,4S,7aR)-4-(tert-Butyl-dimethyl-silanyloxy)-7a-methyl-1-[(S)-1-methyl-prop-ynyl]-octahydro-indene.

MS: (M)+ 330

IR: cm$^{-1}$ 3540;2935; 2873; 2242; 1722; 1589; 1508; 1470; 1457; 1445; 1436; 1361; 1302; 1244; 1142;991; 761.

Typically, the compounds of formula IX, (1R,3aR,4S,7aR)-4-(tert-Butyl-dimethyl-silanyloxy)-7a-methyl-1-[(S)-1-methyl-propynyl]-octahydro-indene (1000 mg; 3.12 mmol) and ethyl-2-iodobenzoat (1290 mg; 4.68 mmol) were dissolved in Piperidin (15 ml). The reaction mixture was degassed and Bis-(triphenylphosphin)-palladium (II)-dichloride (219 mg; 0.312 mmol) and copper-(I)-iodide were added. The reaction mixture was stirred at room temperature for two hours then was heated at 50° C. overnight. The reaction mixture was then poured on chilled aqueous hydrochloric acid, extracted twice with ethyl acetate, washed twice with brine, dried over anhydrous sodium sulfate and the solvent was removed. After flash-chromatography (eluent: hexanes/ethyl-acetate 96/4) the impure adduct was obtained as a brown oil. The brown oil was dissolved in THF (25 ml). Hydrofluoric acid (40% aqueous solution; 13 ml) was added and the reaction mixture was stirred at room temperature for forty hours. The reaction mixture was then poured on chilled brine, extracted twice with ethyl acetate, washed twice with brine, dried over anhydrous sodium sulfate and the solvent was removed. After flash-chromatography (eluent: hexanes/ethyl-acetate 82/18) the compound of formula VI of the above Example 1F, (1R,3aR,4S,7aR)-4-Hydroxy-1-[(S)-3-[2-(carboxylic acid ethyl ester)-phenyl-1-methyl-propynyl]-7a-methyl-octahydro-indene (642 mg; yield: 58%) was obtained as a yellow oil.

G) The following compounds of formula V or VI were obtained from compounds of formula VIII:

EXAMPLE 1G (E)-4-[(R)-3-[(1R,3aR,4S,7aR)-4-Hydroxy-7a-methyl-octahydro-inden-1-yl]-but-1-enyl]-benzoic acid ethyl ester from (E)-(R)-(1R,3aR,4S,7aR) -7a-Methyl-1-[(S)-methyl-3-tributylstannyl-allyl]-octahydro-inden-4-ol.

MS: (M+H)+ 357

IR: cm$^{-1}$ 3522; 2934; 2869; 1715; 1646; 1606; 1456; 1411; 1368; 1275; 1178; 1106; 1068; 1022; 969; 873; 705; 704.

EXAMPLE 2G (E)-2-[(R)-3-[(1R,3aR,4S,7aR)-4-Hydroxy-7a-methyl-octahydro-inden-1-yl]-but-1-enyl]-benzoic acid ethyl ester from (E)-(R)-(1R,3aR,4S,7aR)-7a-Methyl-1-[(S)-methyl-3-tributylstannyl-allyl]-octahydro-inden-4-ol.

MS: (M)$^{30}$ 356

IR: cm$^{-1}$ 3527; 2933; 2869; 1716; 1646; 1602; 1571; 1477; 1449; 1367; 1294; 1251; 1166; 1127; 1074; 1023; 990; 965; 751; 709.

EXAMPLE 3G (E)-3-[(R)-3-[(1R,3aR,4S,7aR)-4-Hydroxy-7a-methyl-octahydro-inden-1-yl]-but-1-enyl]-benzoic acid ethyl ester from (E)-(R)-(1R,3aR,4S,7aR)-7a-Methyl-1-[(S)-methyl-3-tributylstannyl-allyl]-octahydro-inden-4-ol.

MS: (M)+ 356

IR: cm$^{-1}$ 3524; 2934; 2868; 1719; 1648; 1601; 1582; 1443; 1369; 1286; 1201; 1167; 1106; 1025; 965; 752.

EXAMPLE 4G (E)-(1R,3aR,4S,7aR)-1-[(R)-1-Methyl-3-[3-(hydroxy-phenyl)-prop-2-enyl]-7a-methyl-octahydro-inden-4-ol from (E)-(R)-(1R,3aR,4S,7aR) -7a-Methyl-1-[(S)-methyl-3-tributylstannyl-allyl]-octahydro-inden-4-ol.

MS: (M)+ 300

IR: cm$^{-1}$ 3430; 3259; 2940; 2863; 1613; 1579; 1500; 1454; 1364; 1331; 1250; 1159; 1060; 963; 778; 686.

EXAMPLE 5G

E-(1R,3R,4S,7aR)-7a-Methyl-1[(S)-1-methyl-3-[2-(tert-butyl-dimethyl-silanyl-oxy)-phenyl]allyl]-octahydro-inden-4-ol from (E)-(R)-(1R,3aR, 4S,7aR) -7a-Methyl-1-[(R)-methyl-3-tributylstannyl-allyl]-octahydro-inden-4-ol.

NMR (CDCl$_{13}$; J in Hz; 250 MHz): 7.14 (t; J=8.1; 1H); 6.91(dm; J=8.1; 1H); 6.81 (sbr; 1H); 6.67 (dm; J=8.1; 1H); 6.24 (d(AB); J=16.2; 1H); 6.00 (d(AB)d; J=16.2, 9.6; 1H); 4.07 (m; 1H); 2.31–0.86 (m; 13H); 0.99(d; J=6.1; 3H); 0.98 (s; 9H); 0.93(s;3H); 0.19 (s; 3H).

Typically, the compound of formula VIII, (E)-(R)-(1R, 3aR,4S,7aR)-7a-Methyl-1-[(S)-methyl-3-tributylstannyl-allyl]-octahydro-inden-4-ol (437 mg; 0.858 mmol) and ethyl-4-iodobenzoat (249 mg; 0.90 mmol) were dissolved in toluene (8 ml). The reaction mixture was degassed and Bis-(triphenylphosphin)-palladium(II)-dichloride (31 mg; 0.043 mmol) was added and the reaction mixture was heated at 75° C. overnight. The reaction mixture was then poured on chilled brine, extracted twice with ethyl acetate, washed twice with brine, dried over anhydrous sodium sulfate and the solvent was removed. After flash-chromatography (eluent: hexanes/ethyl-acetate 8/2) the compound of formula VI of Example 1G, (E)-4-[(R)-3-[(1R,3aR,4S,7aR)-4-Hydroxy-7a-methyl-octahydro-inden-1-yl]-but-1-enyl]-benzoic acid ethyl ester (182 mg; yield: 60%) was obtained as a brown oil.

In Example 5G, 3-(tert-butyl-dimethyl-silanyloxy)-iodobenzene is utilized instead of ethyl-4-iodobenzoate.

H) The following compound of formula VIII were obtained from compounds of formula VII:

EXAMPLE 1H (E)-(R)-(1R,3aR,4S,7aR) -7a-Methyl-1-[(S)-methyl-3-tributylstannyl-allyl]-octahydro-inden-4-ol from [1R,3aR, 4S,7aR]-7a-Methyl-1-[(S)-1-methyl-prop-2-ynyl]-octahydro-inden-4-ol.

NMR (CDCl$_3$, J in Hz; 250 MHz): 5.74 (m; 2H); 4.08 (m; 1H); 2.18–0.82 (m; 47H).

EXAMPLE 2H (E)-(R)-(1R,3aR,4S,7aR) -7a-Methyl-1-[(R)-methyl-3-tributylstannyl-allyl]-octahydro-inden-4-ol from [1R,3aR, 4S,7aR]-7a-Methyl-1-[(R)-1-methyl-prop-2-ynyl]-octahydro-inden-4-ol.

MS: (M–C$_4$H$_9$)$^+$ 441

IR: cm$^{-1}$ 3408; 2954; 2926; 2870; 1594; 1458; 1374; 1160; 1069; 990; 942; 882.

Typically, the compound of formula VII [1R,3aR,4S, 7aR]-7a-Methyl-1-[(S)-1-methyl-prop-2-nyl]-octahydro-inden-4-ol (494 mg; 2.39 mmol) was dissolved in toluene (16 ml). Then tributyltinhydride (698 ml; 2.63 mmol) and Azobisisobutyronitrile (39 mg; 0.24 mmol) were added and reaction mixture was heated at 80° C. for three hours. The reaction mixture was then poured on chilled brine, extracted twice with ethyl acetate, washed twice with brine, dried over anhydrous sodium sulfate and the solvent was removed. After flash-chromatography (eluent: hexanes/ethyl-acetate 9/1) the compound (E)-(R)-(1R,3aR,4S,7aR) -7a-Methyl-1-[(S)-methyl-3-tributylstannyl-allyl]-octahydro-inden-4-ol (908 mg; yield: 74%) was obtained as a colorless oil.

I) The following compounds of formula VII were obtained from compounds of formula IX:

EXAMPLE 1I

[1R,3aR,4S,7aR]-7a-Methyl-1-[(S)-1-methyl-prop-2-ynyl]-octahydro-inden-4-ol from (1R,3aR,4S,7aR)-4-(tert-Butyl-dimethyl-silanyloxy)-7a-methyl-1-[(S)-1-methyl-propynyl]-octahydro-indene.

MS: (M–CH$_3$)$^+$ 191

IR: cm$^{-1}$ 3429; 3307; 2935; 2872; 2118; 1454; 1374; 1268; 1233; 1163; 1066; 989; 943; 625.

EXAMPLE 2I

[1R,3aR,4S,7aR]-7a-Methyl-1-[(R)-1-methyl-prop-2-nyl]-octahydro-inden-4-ol from(1R,3aR,4S,7aR)-4-(tert-Butyl-dimethyl-silanyloxy)-7a-methyl-1-[(R)-1-methyl-propynyl]-octahydro-indene.

MS: (M)$^+$ 206

IR: cm$^{-1}$ 3356; 3306; 2932; 2879; 2120; 1453; 1376; 1268; 1168; 1066; 990; 946; 643; 621.

Typically, the compound of formula IX, (1R,3aR,4S, 7aR)-4-(tert-Butyl-dimethyl-silanyloxy)-7a-methyl-1-[(S)-1-methyl-propynyl]-octahydro-indene (900 mg; 2.81 mmol) was dissolved in THF (35 ml). Hydrofluoric acid (40% aqueous solution; 18 ml) was added and the reaction mixture was stirred at room temperature for three hours. The reaction mixture was then poured on chilled brine, extracted twice with ethyl acetate, washed twice with brine, dried over anhydrous sodium sulfate and the solvent was removed. After flash-chromatography (eluent: hexanes/ethyl-acetate 82/18) the compound [1R,3aR,4S,7aR]-7a-Methyl-1-[(S)-1-methyl-prop-2-ynyl]-octahydro-inden-4-ol (497 mg; yield: 86%) was obtained as a yellow oil.

J) The following compounds of formula IX were obtained from compounds of formula X:

EXAMPLE 1J (1R,3aR,4S,7aR)-4-(tert-Butyl-dimethyl-silanyloxy)-7a-methyl-1-[(S)-1-methyl-propynyl]-octahydro-indene from (1R,3aR,4S,7aR)-4-(tret-Butyl-dimethyl-silanyloxy)-1-[(S)-3,3-dibromo-1-methyl-allyl]-7a-methyl-octahydro-indene.

MS: (M–tBu)$^+$ 263

IR: cm$^{-1}$ 3312; 2932; 2858; 2120; 1252; 1165; 1083; 1029; 836; 774.

EXAMPLE 2J (1R,3aR,4S,7aR)-4-(tert-Butyl-dimethyl-silanyloxy)-7a-methyl-1-[(R)-1-methyl-propynyl]-octahydro-indene from (1R,3aR,4S,7aR)-4-(tret-Butyl-dimethyl-silanyloxy)-1-[(R)-3,3-dibromo-1-methyl-allyl]-7a-methyl-octahydro-indene.

MS: (M)$^+$ 320

IR: cm$^{-1}$ 3313; 2954; 2931; 2859; 2120; 1469; 1375; 1253; 1166; 1079; 1020; 973; 953; 924; 836; 774; 687; 629.

Typically, the compound of formula X, (1R,3aR,4S,7aR)-4-(tret-Butyl-dimethyl-silanyloxy)-1-[(S)-3,3-dibromo-1-methyl-allyl]-7a-methyl-octahydro-indene (8.94 g; 18.6 mmol) is dissolved in dry THF (80 ml) and cooled to −78° C. Butyllithium (28.6 ml of a 1.6M solution in hexane; 42.8 mmol) is added dropwise. The reaction mixture is allowed to reach room temperature and is then poured on chilled aqueous citric acid. The mixture is extracted twice with ethyl-acetate(150 ml); the organic phase is washed twice with brine (50 ml), dried over sodium sulfate After evaporation of the solvents and flash-chromatography over silica gel (hexanes/ethyl acetate 99:1) the compound (1R,3aR,4S, 7aR)-4-(tert-Butyl-dimethyl-silanyloxy)-7a-methyl-1-[(S)-1-methyl-propynyl]-octahydro-indene (5.85 g; Yield 98%) was obtained as a yellow oil.

K) The following compounds of formula X were obtained from aldehydes of formula XI:

EXAMPLE 1K (1R,3aR,4S,7aR)-4-(tert-Butyl-dimethyl-silanyloxy)-1-[(S)-3,3-dibromo-1-methyl-allyl]-7a-methyl-octahydro-indene from (S)-2-[(1R,3aR,4S,7aR)-4-(tert-Butyl-dimethyl-silanyloxy)-7a-methyl-octahydro-inden-1-yl]-propan-1-al.

MS: (M–tBu)$^+$ 423

IR: cm$^{-1}$ 2932; 2857; 1626; 1467; 1375; 1252; 1165; 1080; 1029; 952; 922; 835; 776.

EXAMPLE 2K (1R,3aR,4S,7aR)-4-(tert-Butyl-dimethyl-silanyloxy)-1-[(R)-3,3-dibromo-1-methyl-allyl]-7a-methyl-octahydro-indene from (R)-2-[(1R,3aR,4S,7aR)-4-(tert-Butyl-dimethyl-silanyloxy)-7a-methyl-octahydro-inden-1-yl]-propan-1-al.

MS: (M–Me)+ 463

IR: cm−1 2930; 2858; 1627; 1465; 1375; 1252; 1167; 1082; 1021; 960; 920; 873; 836; 775; 686.

Typically, tetrabromomethane (16.8 g; 50.6 mmol) is dissolved in dichloromethane (80 ml). Triphenylphosphine (26.5 g; 101.1 mmol) in solution in dichloromethane (40 ml) is added dropwise. The reaction mixture is cooled to −20° C. and the compound (S)-2-[(1R,3aR,4S,7aR)-4-(tert-Butyl-dimethyl-silanyloxy)-7a-methyl-octahydro-inden-1-yl]-propan-1-al (*J. Org Chem:* 1992, 57, 3173 ) in solution in dichloromethane (30 ml) is added dropwise. The reaction mixture is allowed to reach room temperature and is then poured on ice. The mixture is extracted twice with ethyl-acetate (250 ml); the organic phase is washed twice with brine (100 ml), dried over sodium sulfate. After evaporation of the solvents and flash-chromatography over silica gel (hexanes/ethyl acetate 98:2) the compound (1R,3aR,4S,7aR)-4-(tert-Butyl-dimethyl-silanyloxy)-1-[(S)-3,3-dibromo-1-methyl-allyl]-7a-methyl-octahydro-indene (8.94 g; Yield 81%) was obtained as a colorless oil.

L) The starting aldehyde utilized in Example 2K above is obtained as follows:

The alcohol, (R)-2-[(1R,3aR,4S,7aR)-4-(tert-Butyl-dimethyl-silanyloxy)-7a-methyl-octahydro-inden-1-yl]-propan-1-ol (10.00 g; 30.6 mmol) is diluted in dichloromethane (120 ml) and powdered molecular sieve 4 Å (6.35 g) and N-methyl morpholine oxide (6.21 g; 45.9 mmol) are added and the mixture is stirred for 30 minutes. The mixture is cooled to −10° C. and tetrapropyl ammonium perruthenate (538 mg; 1.53 mmol) is added. The reaction mixture is allowed to reach room temperature and stirred for an additional hour. The mixture is purified by chromatography over silicagel using n-hexanes/ethylacetate 98/2 as eluent. One obtains 7.64 g (yield 76.4%) of the intermediate aldehyde: (R)-2-[(1R,3aR,4S,7aR)-4-(tert-butyl-dimethyl-silanyloxy)-7a-methyl-octahydro-inden-1-yl]-propan-al.

M) The starting (R)-alcohol utilized in Example L is obtained as follows:

The aldehyde (S)-2-[(1R,3aR,4S,7aR)-4-(tert-Butyl-dimethyl-silanyloxy)-7a-methyl-octahydro-inden-1-yl]-propan-1-al (7.63 g; 23.5 mmol) is diluted in absolute THF (120 ml) and 1,5-diazabicyclo[4.3.0]non-5-ene (DBN) (2.81 ml; 23.5 mmol) is added. The mixture is heated to reflux for 6 hours. The reaction mixture is poured on a chilled citric acid solution and extracted with ethylacetate. The organic phase is dried over sodium sulfate and the solvents were removed. The 1H NMR of the crude reaction product indicates an approximate 1/1 mixture of the diastereomeric isomers. The crude mixture is diluted in isopropanol (100 ml) and at 0° C. NaBH4 (978 mg; 25.9 mmol) is added. The mixture is stirred half an hour at 0° C. and at RT over night. The reaction mixture is then poured in chilled brine and extracted twice with ethyl-acetate. The organic layer is washed with brine and dried over sodium sulfate. The solvents were removed and the crude product is purified by two consecutive flash-chromatographies (n-hexanes/ethyl-acetate: 95/5). The 20-epi alcohol (R)-2-[(1R,3aR,4S,7aR)-4-(tert-Butyl-dimethyl-silanyloxy)-7a-methyl-octahydro-inden-1-yl]-propan-1-ol is obtained in 41% yield (3.135 g).

MS: (M–Me)+ 311

IR: cm−1 3352; 2931; 2858; 1469; 1374; 1252; 1166; 1081; 1025; 919; 835; 774.

The following compounds of formula I were obtained from the hydroxyketone of formula IVa, (4aR,5R,8aR)-5-((S)-3-[2-(1-hydroxy-1-methyl-ethyl)-phenyl]-1-methyl-prop-2-ynyl)-4a-methyl-octahydro-naphthalen-1-one by protection of the alcohol as trimethylsilyl ether of formula IV, Wittig reaction with a phosphinoxide of formula III, followed by cleavage of the silyl groups by treatment with excess fluoride, according to the experimental procedure given below:

EXAMPLE 27

(7E)-(1R,3R)-23-2(1-Hydroxy-1-methyl-ethyl)-phenyl]-D-homo-19,24-dinor-9,10-seco-chola-5,7-dien-22-yne-1,3-diol

MS: (M)+ 476

NMR: (1H, d, TMS) 0.87 (s, 3H), 1.32 (d, 3H), 1.69 (s, 6H), 1.15–1.85 (m, 14H), 1.9 (m, 3H), 2.2 (m, 2H), 2.49 (dd, 1H), 2.75 (dd, 1H), 2.9 (m, 1H), 3.13 (q, 1H), 3.94 (s, OH), 4.1 (m, 1H), 4.2 (m, 1H), 5.85 (d, 1H), 6.31 (d, 1H), 7.1–7.25 (m, 2H), 7.41 (dxt, 2H).

EXAMPLE 28

(5Z,7E)-(1S,3R)-23-[2-(1-Hydroxy-1-methyl-ethyl)-phenyl]-D-homo-24-nor-9,10-seco-chola-5,7,10(19)-trien-22-yne-1,3-diol

MS: (M)+ 488

NMR: (1H, d, TMS) 0.86 (s, 3H), 1.34 (d, 3H), 1.69 (s, 6H), 1.15–2.0 (m, 17H), 2.31 (dd, 1H), 2.61 (dd, 1H), 2.75 (dd, 1H), 2.9 (M, 1H), 3.13 (q, 1H), 3.94 (s, OH), 4.24 (m, 1H), 4.43 (m, 1H), 4.99 (s, 1H), 5.33 (s, 1H), 6.02 (d, 1H), 6.36 (d, 1H), 7.1–7.25 (m, 2H), 7.41 (dxt, 2H).

EXAMPLE 29

(5Z,7E)-(3S)-23-[2-(1-Hydroxy-1-methyl-ethyl)-phenyl]-D-homo-24-nor-9,10-seco-chola-5,7,10(19)-trien-22-yne-3-ol

MS: (M)+ 472

NMR: (1H, d, TMS) 0.86 (s, 3H), 1.32 (d, 3H), 1.69 (s,6H), 1.15–2.7 (m, 20H), 2.9 (m, 1H), 3.11 (q, 1H), 3.94 (s, OH and 1H), 4.81 (s, 1H), 5.06 (s, 1H), 6.04 (d, 1H), 6.22 (d, 1H), 7.1–7.25 (m, 2H), 7.40 (dxt, 2H).

Typically, the compound of Example 28 was prepared as follows:

a) The hydroxyketone of formula IVa, (4aR,5R,8aR)-5-((S)-3-[2-(1-hydroxy-1-methyl-ethyl)-phenyl]-1-methyl-prop-2-ynyl)-4a-methyl-octahydro-naphthalen-1-one (419 mg, 1.19 mmol) was dissolved in $CH_2Cl_2$ (10 ml) and treated with trimethylsilyl-imidazole (0.889 ml, 6.07 mmol). The mixture was kept at 35–40° C. for 5 h, poured onto crashed ice, extracted twice with ether, washed with water, dried over sodium sulfate and evaporated to dryness. Flash chromatography ($SiO_2$), hexane/AcOEt=9/1) yielded 504 mg of (4aR,5R,8aR)-4a-methyl-5-((S)-1-methyl-3-[2-(1-methyl-1-trimethyl-silanyloxy-ethyl)-phenyl]-prop-2-ynyl)-octahydro-naphthalen-1-one.

b) The phosphinoxide, (3S,5R)-(Z)-[2-[3,5-bis-(tertbutyl-dimethyl-silanyloxy)-2-methylenecyclohexylidene]ethyl]-diphenyl phosphine oxide (563 mg, 0.965 mmol) was dissolved in dry THF (5 ml) and treated at −78° C. with 0.722 ml 1.55 M nBuLi (hexane). 10 minutes later, the above prepared ketone (205 mg, 0.482 mmol), dissolved in a tiny amount of THF, was added to the deep red solution. The reaction temperature was kept at −78° C. for 0.75 h and then slowly allowed to reach 0° C. After 2.5 h the reaction mixture was poured onto crashed ice/NH$_4$Cl, extracted twice with ether, washed with water and brine, dried over sodium sulfate and evaporated to dryness. Flash chromatography (SiO$_2$, hexane/AcOEt=9/1) yielded in the less polar fractions 129 mg of ((5Z,7E)-(1S,3R)-1,3-bis-(tert-butyldimethyl-silanyloxy)-23-[2-(1-methyl-1-trimethylsilanyloxy-ethyl)-phenyl]-D-homo-24-nor-9,10-seco-chola-5,7,10(19)-trien-22-yne as colorless oil and in the more polar ones 111 mg of starting ketone.

c) 619 mg (1.96 mmol) of TBAF trihydrate in 4 ml of THF was dried by stirring at ambient temperature over 0.6 g of 3 Å molecular sieve for 2 h. The resultant solution was then added to the above prepared 129 mg of protected Vitamin D-derivative and the mixture kept for 1.5 h at 50° C. The reaction mixture was then poured onto crashed ice/NH$_4$Cl, extracted twice with ether, washed with water and brine, dried over sodium sulfate and evaporated to dryness. Flash chromatography (SiO$_2$, hexane/AcOEt=1/2) afforded 80 mg of ((5Z,7E)-(1S,3R)-23-[2-(1-hydroxy-1-methyl-ethyl)-phenyl]-D-homo-24-nor-9,10-seco-chola-5,7,10(19)-trien-22-yne-1,3-diol) as colorless gum.

N) The starting hydroxyketone of formula IVa, utilized in paragraph a) above, (4aR,5R,8aR)-5-((S)-3-[2-(1-Hydroxy-1-methyl-ethyl)-phenyl]-1-methyl-prop-2-ynyl)-4a-methyl-octahydro-naphthalen-1-one was prepared from corresponding alcohol-ether of formula XII, (S)-2-[(1R,4aR,5S,8aR)-5-(tert-Butyl-dimethyl-silanyloxy)-8a-methyl-decahydro-naphthalen-1-yl]-propan-1-ol (Example 15 in European Pat. Appl. No. 95117037.2) (RAN 4212/067-00) as follows:

a) Swern reagent was prepared at −60° C. by adding slowly DMSO (0.899 ml, 11.5 mmol, dissolved in 2 ml of CH$_2$Cl$_2$) to oxalylchloride (0.503 ml, 5.85 mmol) in 10 ml of CH$_2$Cl$_2$. 15 Minutes later, (S)-2-[(1R,4aR,5S,8aR)-5-(tert-Butyl-dimethyl-silanyloxy)-8a-methyl-decahydro-naphthalen-1-yl]-propan-1-ol (1.81 g, 5.31 mmol), dissolved in 7 ml of CH$_2$Cl$_2$, was slowly added. After ½ h, NEt$_3$ (5.18 ml, 37.2 mmol) was added and the temperature allowed to reach −25° C. The reaction was quenched by pouring onto crashed ice/NH$_4$Cl, extracted twice with ether, washed with water and brine, dried over sodium sulfate and evaporated to dryness. Flash chromatography (SiO$_2$, hexane/AcOEt=97/3) yielded 1.583 g of (S)-2-[(1R,4aR,5S,8aR)-5-(tert-Butyl-dimethyl-silanyloxy)-8a-methyl-decahydro-naphthalen-1-yl]-propionaldehyde as isomerically pure, colorless oil.

b) CBr$_4$ (3.10 g, 9.35 mmol) was dissolved in 21 ml of CH$_2$Cl$_2$ and treated at −15° C. with Ph$_3$P (4.70 g, 18.7 mmol). 10 Minutes later, the above prepared aldehyde (1.583 g, 4.675 mmol), dissolved in 5 ml of CH$_2$Cl$_2$, was slowly added and allowed to react with the ylide for ½ h. The crude reaction mixture was distributed twice between hexane and EtOH/water=8/2, the upper layer dried over sodium sulfate and the solvent evaporated. Flash chromatography (SiO$_2$, hexane) afforded 2.18 g of tert-Butyl-[(1S,4aR,5R,8aR)-5-((S)-3,3-dibromo-1-methyl-allyl)-4a-methyl-decahydro-naphthalen-1-yloxy]-dimethyl-silane as colorless oil.

c) The above synthesized dibromide (2.18 g, 4.41 mmol) was dissolved in dry THF (26 ml) and treated at −78° C. with nBuLi (9.55 ml [1.5M (hexane)], 14.3 mmol). 60 Minutes later the reaction mixture was poured onto crashed ice/NH$_4$Cl, extracted twice with ether, washed with brine, dried over sodium sulfate and evaporated to dryness. Flash chromatography (SiO$_2$, hexane) yielded 1.37 g of the desired tert-Butyl-dimethyl-[(1S,4aR,5R,8aR)-4a-methyl-5-((S)-1-methyl-prop-2-ynyl)-decahydro-naphthalen-1-yloxy]-silane as pure, colorless oil.

d) The above prepared acetylene (1.37 g, 4.09 mmol), dissolved in 20 ml of piperidine, was mixed under scrupulous exclusion of air with ethyl 2-iodobenzoate (1.69 g, 6.14 mmol), CuI (78 mg, 0.408 mmol), and (Ph$_3$P)$_4$Pd (472 mg, 0.408 mmol) and allowed to react at 50° C. for 2 h. The mixture was poured onto crashed ice/HCl, extracted twice with ether, washed with water and brine, dried over sodium sulfate and evaporated to dryness. Flash chromatography (SiO$_2$, hexane/AcOEt=98/2) gave 1.841 g of 2-((S)-3-[(1S,4aR,5R,8aR) 5-(tert-Butyl-dimethyl-silanyloxy)-8a-methyl-decahydro-naphthalen-1-yl]-but-1-ynyl)-benzoic acid ethyl ester, containing some starting iodo-ester as impurity, which was removed after the next step.

e) Grignard reagent was prepared according to standard procedures starting from MeI (2.27 g, 16 mmol) and Mg turnings (0.365 g, 15 mmol) in 50 ml of dry ether. After cooling to −78° C. 1.437 g (<3 mmol, not corrected) of the above prepared ester, dissolved in 10 ml of dry THF, was added drop by drop and the mixture stirred at room temperature for 2 h. Under cooling and Argon flush, the excess of reagent was carefully destroyed with NH$_4$Cl-solution, the layers were separated, the aqueous phase extracted with ether, the combined organic layers washed with NH$_4$Cl-solution, dried over sodium sulfate and evaporated to dryness. Flash chromatography (SiO$_2$, hexane/AcOEt=93/7) yielded 862 mg of 2-((S)-(3-[(1S,4aR,5R,8aR)-5-(tert-Butyl-dimethyl-silanyloxy)-8a-methyl-decahydro-naphthalen-1-yl]-but-1-ynyl)-phenyl)-propan-2-ol as colorless oil.

f) 2.90 g (9.19 mmol) of TBAF trihydrate in 18 ml of THF was dried by stirring at ambient temperature over 2.5 g of 3 Å molecular sieve for 1.5 h. The resultant solution was then added to the above prepared 862 mg silyl-ether. After stirring during 44 h at 75° C., the reaction mixture was poured onto crashed ice. Usual workup followed by flash chromatography (SiO$_2$, hexane/AcOEt=8/2) yielded in the less polar fractions 174 mg of starting material and in the more polar ones 424 mg of (1S,4aR,5R,8aR)-5-((S)-3-[2-(1-Hydroxy-1-methyl-ethyl)-phenyl]-1-methyl-prop-2-ynyl)-4a-methyl-decahydro-naphthalen-1-ol as yellowish crystals of mp. 126–128° C.

g) 423 mg of the above synthesized alcohol was dissolved in 10 ml of CH$_2$Cl$_2$ and treated with pyridinium dichromate (1.86 g, 4.95 mmol). After stirring for 3 h at ambient temperature the reaction mixture was filtered and then washed thoroughly with ether. The combined organic washings were evaporated to dryness and purified by flash chromatography (SiO$_2$, hexane/AcOEt=8/2) to give 420 mg of (4aR,5R,8aR)-5-((S)-3-[2-(1-Hydroxy-1-methyl-ethyl)-phenyl]-1-methyl-prop-2-ynyl)-4a-methyl-octahydro-naphthalen-1-one as colorless oil.

MS: (M)$^+$ 352

NMR: (1H, d, TMS) 0.95 (s, 3H), 1.35 (d,3H), 1.69 (s, 6H), 1.2–2.2 (m, 12H), 2.35 (m, 2H), 3.13 (q, 1H), 3.80 (s, OH), 7.14–7.3 (m, 2H), 7.37–7.47 (m, 2H).

EXAMPLE 30

The compound of formula I, (7E)-(1R,3R)-23-[2-(1-Hydroxy-1-methyl-ethyl)-phenyl]-D-homo-19,24-dinor-9,10-seco-chola-5,7,17-trien-22-yne-1,3-diol

MS: (M)$^+$ 474

NMR: (1H, d, TMS) 0.95 (s, 3H), 1.42 (d,3H), 1.69 (s, 6H), 1.25–2.3 (m), 2.48 (m, 1H), 2.7–2.9 (m, 2H), 3.42 (q,

1H), 3.84 (s, OH), 4.0–4.2 (m, 2H), 5.81 (m, 1H), 5.91 (d, 1H), 6.31 (d, 1H), 7.1–7.3 (m, 2H), 7.43 (m, 2H).

was prepared following the experimental procedures given in Example 27, 28 and 29, but starting from alcohol-ether of formula XII, (S)-2-[(4aR,5S,8aS)-5-(tert-Butyl-dimethyl-silanyloxy)-8a-methyl-3,4,4a,5,6,7,8,8a-octahydro-naphthalen-1-yl]-propan-1-ol (Example 14 in European Pat. Appl. No. 95117037.2, RAN 4212/067-00).

The following compounds of formula I were obtained from hydroxyketone of formula IVa, (4aR,5R,8aR)-5-((R)-3-[2-(1-hydroxy-1-methyl-ethyl)-phenyl]-1 -methyl-prop-2-ynyl)-4a-methyl-octahydro-naphthalen-1-one, by protection of the alcohol as trimethylsilyl-ether of formula IV, Wittig reaction with a phosphinoxide of formula III, followed by cleavage of the silyl groups by treatment with excess fluoride, according to the experimental procedure described above for the product of Example 28:

EXAMPLE 31

(7E)-(1R,3R,20R)-23-[2-(1-Hydroxy-1-methyl-ethyl)-phenyl]-D-homo-19,24-dinor-9,10-seco-chola-5,7-dien-22-yne-1,3-diol MS: $(M+NH_4)^+$ 494, $(M+Na)^+$ 499

NMR: (1H, d, TMS) 0.74 (s, 3H), 1.20 (d, 3H), 1.71 (s, 6H), 1.2–2.0 (m, 17H), 2.24 (m, 2H), 2.50 (dd, 1H), 2.75 (dd, 1H), 2.88 (m, 1H), 3.10 (dq, 1H), 3.90 (s, OH), 4.0–4.2 (m, 2H), 5.87 (d, 1H), 6.31 (d, 1H), 7.15–7.25 (m, 2H), 7.44 (m, 2H).

EXAMPLE 32

(5Z,7E)-(1S,3R,21R)-23-[2-(1-Hydroxy-1-methyl-ethyl)-phenyl]-D-homo-24-nor-9,10-seco-chola-5,7,10(19)-trien-22-yne-1,3-diol

MS: $(M)^+$ 488

NMR: (1H, d, TMS) 0.74 (s, 3H), 1.20 (d,3H), 1.71 (s, 6H), 1.25–2.05 (m, 17H), 2.32 (dd, 1H), 2.61 (dd, 1H), 2.89 (m, 1H), 3.10 (qd, 1H), 3.90 (s, OH), 4.24 (m, 1H), 4.45 (m, 1H), 5.00 (s, 1H), 5.34 (s, 1H), 6.02 (d, 1H), 6.39 (d, 1H), 7.1–7.3 (m, 2H).

EXAMPLE 33

(5Z,7E)-(3S,21R)-23-[2-(1-Hydroxy-1-methyl-ethyl)-phenyl]-D-homo-24-nor-9,10-seco-chola-5,7,10(19)-trien-22-yne-3-ol

MS: $(M)^{30}$ 472

NMR: (1H, d, TMS) 0.74 (s, 3H), 1.20 (d,3H), 1.71 (s, 6H), 1.25–2.5 (m, 19H), 2.57 (dd, 1H), 2.88 (m, 1H), 3.10 (dq, 1H), 3.91 (s, OH), 3.94 (m, 1H), 4.82 (s(br), 1H), 5.07 (s(br), 1H), 6.03 (d, 1H), 6.22 (d, 1H), 7.1–7.3 (m, 2H), 7.44 (m, 2H).

The starting hydroxyketone of formula IVa (4aR,5R,8aR)-5-((R)-3-[2-(1-Hydroxy-1-methyl-ethyl)-phenyl]-1-methyl-prop-2-ynyl)-4a-methyl-octahydro-naphthalen-1-one utilized for Example 31, 32 and 33 was prepared from (R)-2-[(1R,4aR,5S,8aR)-5 -(tert-Butyl-dimethyl-silanyloxy)-8a-methyl-decahydro-naphthalen-1-yl]-propan-1-ol following similar lines as described in example N) above.

O) The alcohol-ethers of formula XII utilized as starting materials in the above paragraph N), and in Examples 27–33 can be obtained as follows:

a) A solution of 30.1 g (0.13 mole) (4aS,5S)-5-tert-butoxy-4a-methyl-4,4a, 5,6,7,8-hexahydro-2(3H)-naphtalenone in 600 ml tetrahydrofurane was cooled under stirring and Argon atmosphere to −78° C. After dropwise addition of 140 ml (0.14 mole) of L-selectride (1 molar in tetrahydrofurane),the reaction mixture was kept at −78° C. for an additional hour, then warmed to room temperature and kept at this temperature for 4.5 hours. After cooling to −15° C., 12 ml of $H_2O$, 90 ml of 4N NaOH and 100 ml of $H_2O_2$ (30%) were added sequentially and dropwise by keeping the temperature between −10° C. to −15° C. After completed addition the reaction mixture was warmed to room temperature, poured onto water and extracted three times with ethylacetate. The combined organic layers were dried with sodium sulfate and evaporated after filtration to yield 30 g of crude (2S,4aS,5S)-5-tert-butoxy-4a-methyl-2,3,4,4a,5,6,7,8-octahydro-naphtalen-2-ol as an amorphous product shown by thin layer chromatography and NMR to be sufficiently pure for further transformations.

b) To a solution of 13 g (54.54 mMol) (2S,4aS,5S)-5-tert-butoxy-4a-methyl-4,4a,5,6,7,8-octahydro-naphtalen-2-ol in 150 ml tetrahydrofurane were added 20 g (112 mMol) of 1,1-thiocarbonyldiimidazole. The reaction mixture was refluxed for two hours, cooled to room temperature and evaporated in vacuo. The residue was chromatographed over silicagel with hexane/ethylacetate 4/1 and gave 14.8 g of Imidazole-1-carbothioic acid(2S,4aS,5S)-O-(5-tert-butoxy-4a-methyl-2,3,4,4a,5,6,7,8-octahydro-naphtalen-2-yl)ester as an amorphous material.

c) To a stirred solution of 9.95 g (28.5 mMol) imidazole-1-carbothioic acid(2S,4aS,5S)-O-(5-tert-butoxy-4a-methyl-2,3,4,4a,5,6,7,8-octahydro-naphtalen-2-yl)ester in 285 ml toluene kept under argon atmosphere were added 75.7 ml (285 mMol) of tributyltinhydride and 75.7 ml of a one molar solution of triethylborane in tetrahydrofurane. The reaction mixture was heated to 120° C. for 4 hours and additional 20 ml of tributyltinhydride as well as 20 ml of triethylborane solution (one molar in tetrahydrofurane) were added. The reaction mixture was kept at 120° C. for 3 days, cooled to room temperature and evaporated in vacuo. The residue was chromatographed twice over 900 g silicagel with toluene/hexane 1/1 to yield 4.3 g of pure (4S,4aS)-4-tert-Butoxy-4a-methyl-1,2,3,4,4a,5,6,7-octahydro-naphtalene (liquid).

d) A solution of 6.15 g (27.6 mMol) of (4aS,4aS)-5-tert-butoxy-4a-methyl-1,2,3,4,4a,5,6,7-octahydro-naphtalene in 180 ml tetrahydrofurane was cooled under argon atmosphere and stirring to 0° C. 55.3 ml (55.3 mMol) of a one molar solution of borane in tetrahydrofurane was added, the reaction mixture kept for an additional hour at 0° C., warmed to room temperature and kept stirring overnight. After cooling to 0° C., 421 ml of water were added dropwise, followed by addition of 25.3 g $NaBO_3.4H_2O$. The suspension was stirred at room temperature for 4 hours, then the reaction mixture was extracted three times with diethylether. The combined organic phases were washed once with brine,dried over sodium sulfate and evaporated in vacuo to yield 12.07 g of crude product, which was chromatographed over 500 g silicagel with hexane/ethylacetate 4/1 to give 3.4 g of a 2:1 mixture of (1S,4aS,5S,8aS)-and (1R,4aS,5S,8aR)-5-tert-butoxy-4a-methyl-decahydro-naphtalen-1-ol as an oily material.

e) To a solution of 3.4 g (14.1 mMol) of (1RS,4aS,5S, 8aRS)-5-tert-butoxy-4a-methyl-decahydro-naphtalen-1-ol in 34 ml methylenechloride was added under stirring 3.66 g (17.0 mMol) of pyridiniumchlorochromate and the reaction mixture was kept under stirring overnight. Then the reaction was diluted with 33 ml diethylether, kept stirring for 15 minutes and filtered over florisil. The filtrate was evaporated to dryness in vacuo and the residue dissolved in 33 ml of tetrahydrofurane. Under stirring and argon atmosphere 1.65 ml of a one molar solution of potassium-tertio-butoxyde in tetrahydrofurane was added and the reaction was kept overnight. This equilibration is monitored by TLC (silicagel, hexane/ethylacetate 4/1), which shows the almost complete disappearance of one of the two epimers. The reaction mixture is evaporated in vacuo to dryness, the residue is taken up in water and extracted three times with diethylether. The combined organic phase is washed with water and brine, dried over sodium sulfate and evaporated in vacuo. The residue is chromatographed over 120 g of silicagel with hexane/ethylacetate 9/1 to yield 2.39 g (71%) of pure (4aS,5S,8aR)-5-tert-butoxy-4a-methyl-octahydro-naphtalen-1-one.

An analytical sample was obtained by cristallisation from hexane with a m.p. of 78–79° C.

f) A solution of 2.12 g (8.9 mMol) of(4aS,5S,8aR)-5-tert-Butoxy-4a-methyl-octahydro-naphtalen-1-one in 44.5 ml tetrahydrofurane was cooled to −78° C. and 9.8 ml (9.8 mnMol) of a one molar solution of L-selectride in tetrahydrofurane was added dropwise under stirring and argon atmosphere. The reaction mixture was kept at this temperature for an additional hour, warmed to room temperature and kept overnight. The temperature was then lowered to −15° C. and 0.17ml of H20 were added dropwise. This was followed by dropwise addition of 7.60 ml 3N NaOH and 6.36 ml of $H_2O_2$. The reaction temperature is kept between −10 to −15° C. The reaction mixture is then poured into water and extracted three times with ethylacetate. The combined organic extracts are washed with brine and evaporated in vacuo to dryness. The residue is chromatographed over 120 g of silicagel with hexane/ethylacetate 4/1 to yield 1.03 g (48%) of pure (1S,4aS,5S,8aR)-5-tert-Butoxy-4a-methyl-decahydronaphtalen-1-ol as an amorphous product.

g) A solution of 4.11 g (17.1 mMol) of(1S,4aS,5S,8aR)-5-tert-butoxy-4a-methyl-decahydro-naphtalen-1-ol and 313.6 mg (2.6 mMol) of 4-dimethyl-aminopyridine in 26 ml of pyridine is treated with 13 ml of acetic anhydride under stirring and argon atmosphere for two hours. The reaction mixture is poured on ice-water and extracted three times with diethylether. The combined organic layer is washed twice with water, dried over sodium sulfate and evaporated in vacuo to yield 1.26 g of crude product which is chromatographed over 60 g of silicagel with hexane/ethylacetate 9/1 to give 4.64 g (91%) of acetic acid(1S,4aS,5S,8aR)-5-tert-butoxy-4a-methyl-decahydro-naphtalen-1-yl ester as an amorphous pure product.

h) A solution of 4.08 g (14.45 mMol) of acetic acid (1S,4aS,5S,8aR)-5-tert-Butoxy-4a-methyl-decahydronaphtalen-1-yl ester in 7.25 ml of carbon tetrachloride is treated dropwise under stirring and argon atmosphere with 2.56 ml (18.8 mMol) of trimethylsilyljodide by keeping room temperature. After completed addition the reaction mixture is stirred for another 30 minutes, then 1.79 ml of methanol are added and the reaction kept for 15 minutes. The reaction mixture is evaporated in vacuo to dryness to yield 5.52 g. The residue is chromatographed over 500 g of silicagel with hexane/ethylacetate 4/1 to give 2.88 g (88%) of pure acetic acid (1S,4aS,5S,8aR)-5-hydroxy-4a-methyl-decahydronaphtalen-1-yl ester.

i) 3.73 g (17.3 mMol) of pyridinium chlorochromate is added under stirring to a solution of 3.25 g (14.35 mMol) of acetic acid (1S,4aS,5S,8aR)-5-hydroxy-4a-methyl-decahydro-naphtalen-1-yl ester in 32.5 ml of dichloromethane. The reaction mixture is stirred overnight, diluted with 70 ml of diethylether, stirred for 15 minutes and filtered over florisil using diethylether for thorough elution. Evaporation in vacuo yields 3.34 g of a residue, which is chromatographed over 200 g of silicagel with hexane/ethylacetate 4/1 to give 3.02 g (94%) of pure acetic acid (1S,4aS,8aR)-4a-methyl-5-oxo-decahydronaphtalen-1-yl ester as an oil.

j) A solution of 2.99 g (13.3 mMol) of acetic acid (1S,4aS,8aR)-4a-methyl-5-oxo-decahydro-naphtalen-1-yl ester in 13.3 ml of ethanol is treated under stirring and argon atmosphere with sodium ethylate prepared from 0.67 g (29.4 gatom) of sodium and 29.4 ml of ethanol and the reaction mixture is kept overnight. The solvent is evaporated in vacuo to dryness, the residue is taken up in water and after cooling to 0° C., the pH is adjusted to 3–4 with 1N HCl. After extracting three times with diethylether, the combined organic extract is washed with brine, dried with sodium sulfate and the solvent is evaporated in vacuo . The residue is triturated with hexane, the cristals are filtered off and dried: 1.07 g (95%) of pure (4aR,5S,8aS)-5-hydroxy-8a-methyl-octahydro-naphtalen-1-one, m.p.: 109.5–111° C.

k) To a solution of 2.3 g (12.6 mMol) of (4aR,5S,8aS)-5-hydroxy-8a-methyl-octahydro-naphtalen-1-one in 63 ml of dimethylformamide are added under stirring and argon atmosphere 3.74 g (24.8 mMol) of tertio-butyl-dimethyl-silylchloride and 1.94 g (28.5 mMol) of imidazole. The reaction mixture is heated to 100° C. for 4 hours, then additional 3.74 g of tert-butyl-dimethylsilylchloride and 1.94 g of imidazole are added and the reaction mixture is kept overnight at 100° C. The reaction mixture is poured onto ice-water and extracted three times with diethylether. The combined organic extract is washed once with water and brine, dried over sodium sulfate and evaporated in vacuo. The residue is chromatographed over 250 g of silicagel with hexane/ethylacetate 9/1 to yield 3.17 g (85%) of low melting cristalline (4aR,5S,8aS)-5-(tert-butyl-dimethyl-silanyloxy)-8a-methyl-octahydro-naphtalen-1-one.

l) A suspension of 11.8 g (31.7 mMol) of ethyltriphenylphosphoniumbromide in 64 ml of tetrahydrofurane is treated under stirring and argon atmosphere with 31.9 ml of a one molar solution of potassiumtertiobutylate and the resulting orange suspension treated with a solution of 3.17 g (10.7 mMol) of(4aR,5S,8aS)-5-(tert-butyl-dimethyl-silanyloxy)-8a-methyl-octahydro-naphtalen-1-one in 64 ml of tetrahydrofurane and kept at room temperature for 3 hours. An additional 11.8 g (31.7 mMol) of ethyltriphenylphosphoniumbromide and 31.9 ml of a one molar solution of potassiumtertiobutylate in tetrahydrofurane are added and the reaction mixture kept overnight. Isobutyraldehyde (5.4 ml) is added, the reaction is stirred for 10 minutes, diluted with diethylether and filtered over Florisil using diethylether as eluent. After evaporation in vacuo, the residue (4.79 g) is chromatographed over 120 g of silicagel with hexane to yield 3.15 g (95%) of pure (1S,4aS,8aR)-tert-butyl-(5-ethylidene-4a-methyl-decahydro-naphtalen-1-yloxy)-dimethyl-silane (E/Z 4/1) as an oil.

m) To a stirred solution of 3.11 g (10.1 mMol) of (1S,4aS,8aR)-tert-Butyl-(5-ethylidene-4a-methyl-decahydro-naphtalen-1-yloxy)-dimethylsilane in 125 ml of toluene are added 0.33 g (11.1 mMol) of finely powdered paraformaldehyde. The reaction mixture is cooled to 0° C. and 12.56 ml of a one molar solution of dimethylaluminumchloride in hexane are added and kept for one hour at this temperature. The reaction mixture is stirred at room temperature overnight, diluted with diethylether, washed with 1N HCl and with water, then dried over sodium sulfate and evaporated in vacuo. The residue is chromatographed over a medium pressure 250 g silicagel column with hexane/ethylacetate 9/1 to yield 2.31 g (67.5%) of pure (S)-2-[(4aR, 5S,8aS)-5-(tert-butyl-dimethyl-silanyloxy)-8a-methyl-3,4, 4a,5,6,7,8,8a-octahydro-naphtalen-1-yl]-propan-1-ol as an oil. By running the reaction with $BF_3 \cdot Et_2O$ in $CH_2Cl_2$ small amounts of the (R)-epimer, the starting material of Examples 31–33 can be isolated.

n) To a solution of 2.27 g (6.7 mMol) of (S)-2-[(4aR,5S,8aS)-5-(tert-Butyl-dimethyl-silanyloxy)-8a-methyl-3,4,4a,5,6,7,8,8a-octahydro-naphtalen-1-yl]-propan-1-ol in 22.7 ml of ethylacetate were added 227 mg of Pd/C 10% and 227 mg of sodium bicarbonate. The reaction mixture was stirred under hydrogen atmosphere overnight, filtered over Speedex using ethylacetate for washing thoroughly and the solvent evaporated in vacuo. The residue was chromatographed over a 250 g Lobar column with hexane/ethylacetate 9/1 to yield 2.18 g (95.5%) of (S)-2-[(1R,4aR,5S,8aR)-5-(tert-butyl-dimethyl-silanyloxy)-8a-methyl-decahydro-naphtalen-1-yl]-propan-1-ol as an oily product.

Pharmacological activities of the compounds of formula I can be demonstrated by the following test procedures:

EXAMPLE I
Calcium Liability Tolerance Test in Mice

By giving a global picture of calcemic liability, this assay indicates that the claimed compounds are well-tolerated and have therefore a low toxicity level. Profound changes in calcium homeostasis strongly affect the weight development of the animals. This parameter is used as a primary test for tolerance. It is desirable that vitamin D activity does not have a toxic effect on calcium metabolism. A well known measure of this effect is calcium liability, which is measured by weight loss during treatment. In accordance with known methods, mice (25–30 g body weight) received daily subcutaneous (s.c.) administrations of the vitamin D derivative for 4 consecutive days. Body weight was registered just before and at the end of a 5 day treatment period. The "highest tolerated dose" (HTD s.c.) in mice is the dose which results in zero weight gain during this treatment period.

For the well known antipsoriatic compound 1,25-dihydroxycholecalciferol (calcitriol) an HTD s.c. of 0.5 µg/kg was observed. In comparison thereto, for compounds of formula I, HTD s.c. figures ranging from 4, 5, 12 and 100 µg/kg for four well tolerated compounds, up to 6800, 7000, 7500 and 8500 µg/kg for the four best tolerated compounds were observed.

From the above results, it can be seen that the compounds of formula I are better tolerated than calcitriol.

EXAMPLE II
Activity Assay Hyperproliferative Disorders

In order to assess whether the better tolerance of the compounds is due to poor activity or non-bioavailability or whether it is due to better activity of the compounds when compared to calcitriol the following assay has been performed.

Orally administered vitamin D analogues can lead to epidermal thickening (acanthosis) in hairless mice. This effect on normal skin is considered to be indicative for a beneficial effect on diseased skin, since the known antipsoriatics such as calcitriol show this effect on normal mouse skin. Compounds of formula I were tested for 4 days at different dosages in order to detect compounds which show this epidermal effect at subtoxic and non-toxic doses (dosage leading to slight or no weight loss). Calcitriol itself could not be dosed for 4 days high enough to obtain this skin effect. The calcitriol data were obtained from animals treated for three days.

Hairless mice (Moro hr/hr) received daily administrations of the test compound in arachis oil by gavage for 4 days, using 2–5 different dosages (3 fold increments; 2 animals per dosage group). The mice were sacrificed at day 5 and skin biopsies were taken, fixed in formalin and treated for histological evaluation. The epidermal thickness was measured at standard magnification using an occular grid. Daily measurements of body weight allows to judge toxicity (calcemic liability) and determine the non-toxic dose level defined as the dose which is tolerated without weight loss.

The results in the table below show that the instant compounds, although less potent, are far superior to calcitriol due to a better ratio between the effective dose and the maximal tolerated dose (HTDp.o.) pointing to a greater therapeutic window between skin effect ($ED_{50}$) and toxic calcemic effects which then allows effective dosing in men devoid of side effects.

| compound | $ED_{50}$ | HTDp.o. | ratio $ED_{50}/HTD$ | TI shift |
|---|---|---|---|---|
| calcitriol | 500 | 1 | 500 | 1 |
| Example 6 | 2500 | 40 | 63 | 8 |
| Example 14 | 7000 | 1000 | 7 | 71 |
| Example 16 | 10000 | 2000 | 5 | 100 |

$ED_{50}$: dose (µg/kg) causing half-maximal epidermal thickening
HTDp.o.: highest tolerated oral dose (µg/kg) without weight loss
TI shift: shift in "therapeutic index", is defined as ratio $ED_{50}/HTD$ for calcitriol divided by the ratio $ED_{50}/HTP$ for the test compound The above results indicate that the compounds of this invention may be an effective treatment for hyperproliferative skin disorders. Here, the $ED_{50}$ of the compounds of this invention at the doses tested indicates that these compounds are able to cause epidermal thickening and that the therapeutic window is better than for calcitriol, which has proven an effective antipsoriatic drug, however, at a higher toxicity.

The compounds of formula I as described above can be administered orally, for the treatment of hyperproliferative skin diseases such as psoriasis, basal cell carcinomas, disorders of keratinization, and keratosis, or for the treatment of neoplastic diseases such as leukemia, or for the treatment of diseases which require modulation of the immune system, such as transplant rejection, graft vs. host disease, or for the treatment of osteoporosis and hyperparathyroidism, to warmblooded animals which need such treatment. More specifically, the compounds of formula I as described above can be administered orally to an adult human in dosages that are—dependent of the compound administered—in the range of about 0.5 to 2000 µg per day for the treatment of the above diseases.

Accordingly, this invention is directed to a method for treating or preventing vitamin D dependent disorders, particularly psoriasis, basal cell carcinomas, disorders of keratinization and keratosis, leukemia, osteoporosis, hyperparathyroidism accompanying renal failure, transplant rejection and graft vs. host disease which comprises administering to a patient suffering from a vitamin D dependent disorder a pharmaceutical composition comprising a compound of formula I in an amount effective to treat or prevent the disorder. In a preferred method, the disorder is a hyperproliferative disorder. A particularly preferred method treats psoriasis.

The compounds of formula I as described above can be administered topically, for the treatment of hyperproliferative skin diseases such as psoriasis, to warmblooded animals which need such treatment. More specifically, the compounds of formula I as described above can be administered topically in dosages that are in the range of about 0.5 to 1000 μg per gram of topical formulation per day, for the treatment of the above diseases. Particular ranges of about 5 to 15, 20 to 100, and 500 to 1000 μg per day are preferred.

The dosage of the compounds of formula I can vary within wide limits depending on the illness to be treated, the age and the individual condition of the patient and on the mode of administration and will, of course, be fitted to the individual requirements in each particular case. A skilled practitioner will readily determine a suitable dosage based on these parameters and on the degree to which the patient's condition is ameliorated during the course of treatment.

This invention is also directed to pharmaceutical compositions which comprise an amount of the compound of formula I effective for the treatment or prevention of vitamin D dependent disorders, particularly psoriasis, basal cell carcinomas, disorders of keratinization and keratosis, leukemia, osteoporosis, hyperparathyroidism accompanying renal failure, transplant rejection and graft vs. host disease and a pharmaceutically acceptable carrier. A preferred disorder is hyperproliferative disorder, in particular psoriasis.

Oral dosage forms comprising compounds of formula I of the invention may be incorporated in capsules, tablets and the like with any known pharmaceutically acceptable carrier materials. Illustrative of such carrier materials which may be incorporated into capsules, and the like are the following: a binder such as gum tragacanth, acacia, corn starch, or gelatin; an excipient such as dicalcium phosphate; a disintegrating agent such as corn starch, potato starch, algenic acid, and the like; solvents such as water, a lubricant such as magnesium stearate, a sweetening agent such as sucrose, lactose, or saccharin; a flavoring agent such as peppermint, oil of wintergreen or cherry. Various other materials may be present as coating or to otherwise modify the physical form of the dosage unit. For instance, tablets may be coated with shellac, sugar, or both. A syrup or elixir may contain the active compound, sucrose as a sweetening agent, methyl and propyl parabens as preservatives, a dye, and a flavoring such as cherry or orange flavor.

Topical dosage forms comprising compounds of formula I of the invention include: ointments and creams encompassing formulations having oleaginous, absorbable, water-soluble and emulsion-type bases such as petrolatum, lanolin, polyethylene glycols and the like. Lotions are liquid preparations and vary from simple solutions to aqueous or hydroalcoholic preparations containing finely divided substances. Lotions can contain suspending or dispersing agents, for example, cellulose derivatives such as ethyl cellulose, methyl cellulose, and the like; gelatin or gums, which incorporate the active ingredient in a vehicle made up of water, alcohol, glycerin and the like. Gels are semi-solid preparations made by gelling a solution or suspension of the active ingredient in a carrier vehicle. The vehicles, which can be hydrous or anhydrous, are gelled using a gelling agent, such as, carboxy polymethylene, and neutralized to a proper gel consistency with the use of alkalies, such as, sodium hydroxide and amines, such as, polyethylenecocoamine.

As used herein, the term "topical" denotes the use of the active ingredient, incorporated in a suitable pharmaceutical carrier, and applied at the site of the disorder for the exertion of local action. Accordingly, the topical composition includes those pharmaceutical forms in which the compound is applied externally by direct contact with the skin. The topical dosage forms comprise gels, creams, lotions, ointments, powders, aerosols and other conventional forms for applying medication to the skin obtained by admixing the compounds of formula I with known pharmaceutical topical carrier materials.

The following pharmaceutical compositions can be prepared in a manner known per se:

Example A

| Soft Gelatine Capsule | mg/Capsule |
|---|---|
| Compound I | 0.0001-1 |
| Butylated Hydroxytoluene (BHT) | 0.016 |
| Butylated Hydroxyanisole (BHA) | 0.016 |
| Fractionated Coconut Oil (Neobee M-5) or Miglyol 812   q.s. | 160.0 |

Example B

| Soft Gelatine Capsule | mg/Capsule |
|---|---|
| Compound I | 0.0001-1 |
| a-Tocopherol | 0.016 |
| Miglyol 812   q.s. | 160.0 |

Example C

| Topical Cream | mg/g |
|---|---|
| Compound I | 0.005-1 |
| Cetyl Alcohol | 1.5 |
| Stearyl Alcohol | 2.5 |
| Span 60 (Sorbitan monostearate) | 2.0 |
| Arlacel 165 (Glyceryl monostearate and polyoxyethylene glycol stearate blend) | 4.0 |
| Tween 60 (polysorbate 60) | 1.0 |
| Mineral Oil | 4.0 |
| Propylene Glycol | 5.0 |
| Propylparaben | 0.05 |
| BHA 0.05 | |
| Sorbitol Solution | 2.0 |
| Edetate Disodium | 0.01 |
| Methylparaben | 0.18 |
| Distilled Water | q.s. |

Example D

| Topical ointment | mg/g |
|---|---|
| Compound I | 0,005-1 |
| Propylenglycol | exc. ad ung. pro 1 g |

What is claimed is:

1. A compound of formula (I)

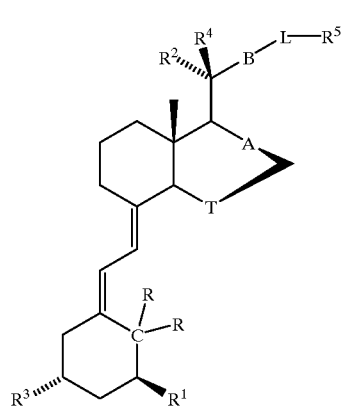

wherein A is a single or double bond; B is $CH_2CH_2$, $CH=CH$, or $C\equiv C$; T is $CH_2$ or $CH_2CH_2$; $R^1$ and $R^3$ are H or OH; $C(R,R)$ is $CH_2$ or $C=CH_2$; $R^2$ is $CH_3$ and $R^4$ is H, or $R^2$ is H and $R^4$ is $CH_3$; L is phenyl and $R^5$ is OH or $C(C_{1-4}\text{-alkyl})_2OH$ or L—$R^5$ is 2-furyl which is 5-substituted by $C(C_{1-4}\text{-alkyl})_2OH$, with the proviso that when L is phenyl; A is a single bond; B is $C\equiv C$; T is $CH_2$; $R^1$ and $R^3$ are OH; $C(R,R)$ is $C=CH_2$; $R^2$ is $CH_3$; $R^4$ is H; and $R^5$ is $C(CH_3)_2OH$; then $R^5$ is in the ortho or para position.

2. A compound of claim 1

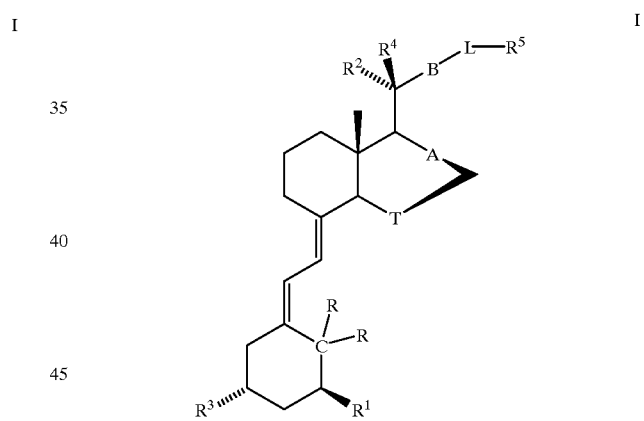

wherein A is a single bond; B is $CH_2CH_2$, $CH=CH$, or $C\equiv C$; T is $CH_2$ or $CH_2CH_2$; $R^1$ and $R^3$ are H or OH; $C(R,R)$ is $CH_2$ or $C=CH_2$; $R^2$ is $CH_3$ and $R^4$ is H, or $R^2$ is H and $R^4$ is $CH_3$; L is phenyl and $R^5$ is OH or $C(C_{1-4}\text{-alkyl})_2OH$ or L—$R^5$ is 2-furyl which is 5-substituted by $C(C_{1-4}\text{-alkyl})_2OH$, with the proviso that when L is phenyl; B is $C\equiv C$; T is $CH_2$; $R^1$ and $R^3$ are OH; $C(R,R)$ is $C=CH_2$; $R^2$ is $CH_3$; $R^4$ is H; and $R^5$ is $C(CH_3)_2OH$; then $R^5$ is in the ortho or para position.

3. A compound of claim 1

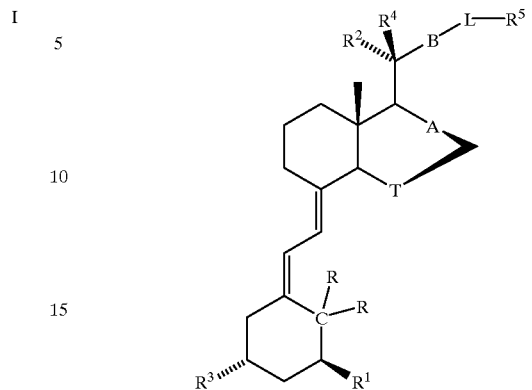

wherein A is a single or double bond; B is $CH_2CH_2$, $CH=CH$, or $C\equiv C$; T is $CH_2$; $R^1$ and $R^3$ are H or OH; $C(R,R)$ is $CH_2$ or $C=CH_2$; $R^2$ is $CH_3$ and $R^4$ is H, or $R^2$ is H and $R^4$ is $CH_3$; L is phenyl and $R^5$ is OH or $C(C_{1-4}\text{-alkyl})_2OH$ or L—$R^5$ is 2-furyl which is 5-substituted by $C(C_{1-4}\text{-alkyl})_2OH$, with the proviso that when L is phenyl; A is a single bond; B is $C\equiv C$; $R^1$ and $R^3$ are OH; $C(R,R)$ is $C=CH_2$; $R^2$ is $CH_3$; $R^4$ is H; and $R^5$ is $C(CH_3)_2OH$; then $R^5$ is in the ortho or para position.

4. A compound of claim 1 wherein A is a single or double bond; B is $CH_2CH_2$, $CH=CH$, or $C\equiv C$; T is $CH_2$ or $CH_2CH_2$; $R^1$ is H or OH and $R^3$ is OH; $C(R,R)$ is $CH_2$ or $C=CH_2$; $R^2$ is $CH_3$ and $R^4$ H, or $R^2$ is H and $R^4$ is $CH_3$; L is phenyl and $R^5$ is OH or $C(C_{1-4}\text{-alkyl})_2OH$ or L—$R^5$ is 2-furyl which is 5-substituted by $C(C_{1-4}\text{-alkyl})_2OH$, with the proviso that when L is phenyl; A is a single bond; B is $C\equiv C$; $R^1$ and $R^3$ are OH; $C(R,R)$ is $C=CH_2$; $R^2$ is $CH_3$; $R^4$ is H; and $R^5$ is $C(CH_3)_2OH$; then $R^5$ is in the ortho or para position.

5. A compound of claim 1

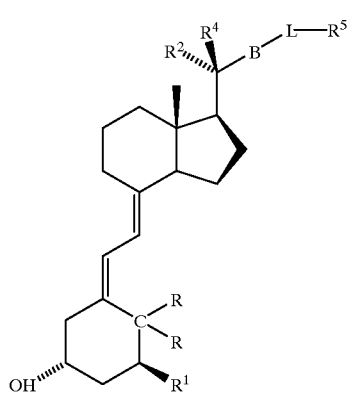
Ia wherein B is $CH_2CH_2$, $CH=CH$, or $C\equiv C$; $R^1$ is H or OH; C(R,R) is $CH_2$ or $C=CH_2$; $R^2$ is $CH_3$ and $R^4$ is H, or $R^2$ is H and $R^4$ is $CH_3$; L is phenyl and $R^5$ is OH or $C(C_{1-4}\text{-alkyl})_2OH$ or L—$R^5$ is 2-furyl which is 5-substituted by $C(C_{1-4}\text{-alkyl})_2OH$, with the proviso that when L is phenyl; B is $C\equiv C$; $R^1$ is OH; C(R,R) is $C=CH_2$; $R^2$ is $CH_3$; $R^4$ is H; and $R^5$ is $C(CH_3)_2OH$; then $R^5$ is in the ortho or para position.

6. A compound of claim 5

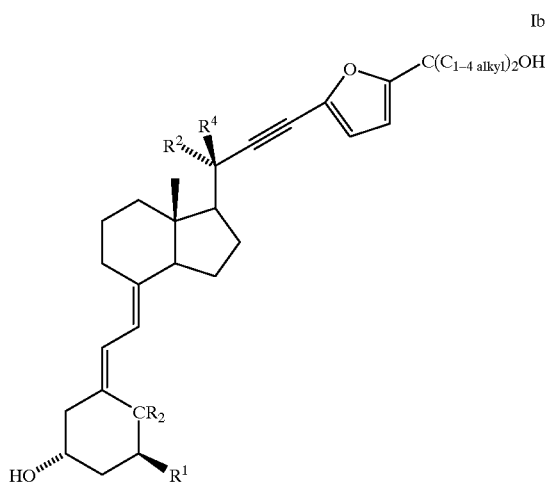
Ib wherein $R^1$ is H or OH; $R^2$ is $CH_3$ and $R^4$ is H or $R^2$ is H and $R^4$ is $CH_3$; and C(R,R) is $CH_2$ or $C=CH_2$.

7. A compound of claim 6 wherein $R^2$ is $CH_3$ and $R^4$ is H.

8. A compound of claim 7 wherein $C(C_{1-4}\text{-alkyl})_2OH$ is $C(CH_3)_2OH$.

9. A compound of claim 8 which is:

(7E)-(1R,3R)-23-[5-(1-hydroxy-1-methyl-ethyl)-furan-2-yl]-19,24-dinor-9,10-seco-chola-5,7-dien-22-yne-1,3-diol.

10. A compound of claim 5

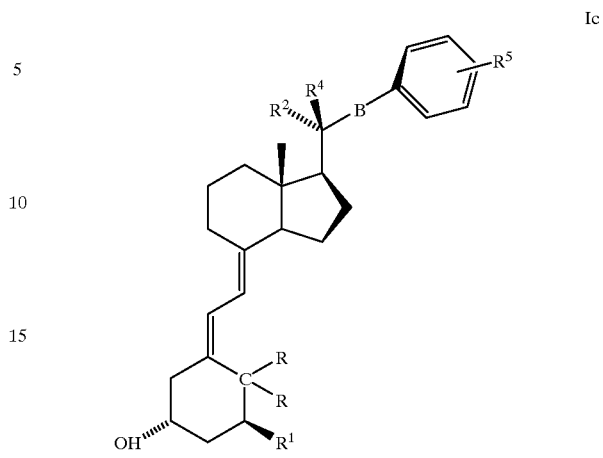
Ic wherein B is $CH_2CH_2$, $CH=CH$, or $C\equiv C$; $R^1$ is H or OH; C(R,R) is $CH_2$ or $C=CH_2$; $R^2$ is $CH_3$ and $R^4$ is H, or $R^2$ is H and $R^4$ is $CH_3$; and $R^5$ is OH or $C(C_{1-4}\text{-alkyl})_2OH$; with the proviso that when B is $C\equiv C$; $R^1$ is OH; C(R,R) is $C=CH_2$; $R^2$ is $CH_3$; $R^4$ is H; and $R^5$ is $C(CH_3)_2OH$; then $R^5$ is in the ortho or para position.

11. A compound of claim 10 wherein B is $CH_2CH_2$.
12. A compound of claim 10 wherein B is $CH=CH$.
13. A compound of claim 10 wherein B is $C\equiv C$.
14. A compound of claim 10 wherein $R^5$ is $C(CH_3)_2OH$.
15. A compound of claim 10 wherein $R^5$ is OH.
16. A compound of claim 10 wherein $R^2$ is $CH_3$ and $R^4$ is H.
17. A compound of claim 10 wherein $R^2$ is H and $R^4$ is $CH_3$.
18. A compound of claim 16 wherein $R^1$ is OH.
19. A compound of claim 1

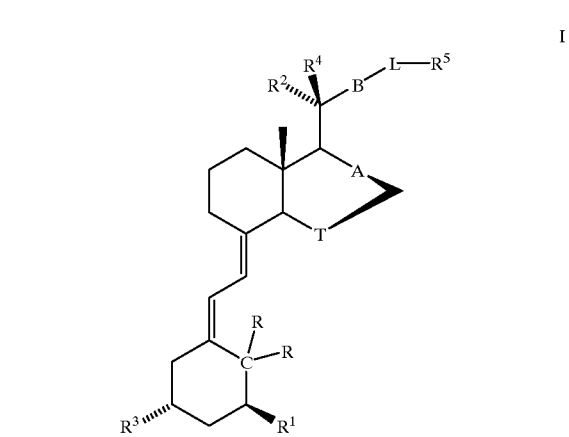
I wherein A is a single or double bond; B is $CH_2CH_2$, $CH=CH$, or $C\equiv C$; T is $CH_2$ or $CH_2CH_2$; $R^1$ and $R^3$ are H or OH; C(R,R) is $CH_2$ or $C=CH_2$; $R^2$ is $CH_3$ and $R^4$ is H, or $R^2$ is H and $R^4$ is $CH_3$; L is phenyl and $R^5$ is OH or $C(C_{1-4}\text{-alkyl})_2OH$; with the proviso that when A is a single bond; B is $C\equiv C$; T is $CH_2$; $R^1$ and $R^3$ are OH; C(R,R) is $C=CH_2$; $R^2$ is $CH_3$; $R^4$ is H; and $R^5$ is $C(CH_3)_2OH$; then $R^5$ is in the ortho or para position.

20. A compound of claim 19 wherein $R^5$ is $C(CH_3)_2OH$.
21. A compound of claim 20 wherein $R^3$ is OH.

22. A compound of claim 21

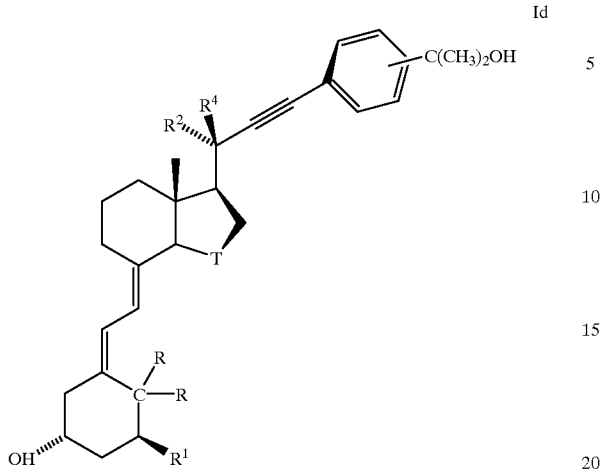

wherein T is $CH_2$ or $CH_2CH_2$; $R^1$ is H or OH; C(R,R) is $CH_2$ or $C=CH_2$; $R^2$ is $CH_3$ and $R^4$ is H, or $R^2$ is H and $R^4$ is $CH_3$; with the proviso that when T is $CH_2$; $R^1$ is OH; C(R,R) is $C=CH_2$; and $R^2$ is $CH_3$; $R^4$ is H; then $R^5$ is in the ortho or para position.

23. A compound of claim 22 wherein T is $CH_2CH_2$.
24. A compound of claim 22 wherein T is $CH_2$.
25. A compound of claim 24 wherein $R^1$ is OH.
26. A compound of claim 25 which is:
  (7E)-(1R,3R,20R)-23-[2-(1-Hydroxy-1-methyl-ethyl)-phenyl)-19,24-dinor-9,10-seco-chola-5,7-dien-22-yne-1,3-diol.
27. A compound of claim 21 wherein B is $CH_2CH_2$, or $C\equiv C$.
28. A compound of claim 27 wherein $R^1$ is OH.
29. Compounds of claim 28 which are
  (7E)-(1R,3R)-23-[2-(1-Hydroxy-1-methyl-ethyl)-phenyl]-19,24-dinor-9,10-seco-chola-5,7-dien-1,3-diol,
  (7E)-(1R,3R)-23-[2-(1-hydroxy-1-methyl-ethyl)-phenyl]-19,24-dinor-9,10-seco-chola-5,7-dien-22-yne-1,3-diol,
  (7E)-(1R,3R)-23-[3-(1-hydroxy-1-methyl-ethyl)-phenyl]-19,24-dinor-9,10-seco-chola-5,7-dien-1,3-diol,
  (5Z,7E)-(1S,3R,20R)-23-[2-(1-hydroxy-1-methyl-ethyl)-phenyl)-24-nor-9,10-seco-chola-5,7,10(19)-trien-22-yne-1,3-diol,
  (7E)-(1R,3R,20S)-23-[3-(1-hydroxy-1-methyl-ethyl)-phenyl)-19,24-dinor-9,10-seco-chola-5,7-dien-1,3-diol,
  (7E)-(1R,3R)-23-[2-(1-hydroxy-1-methyl-ethyl)-phenyl]-D-homo-19,24-dinor-9,10-seco-chola-5,7,17-trien-22-yne-1,3-diol,
  (5Z,7E)-(1S,3R,21R)-23-[2-(1-hydroxy-1-methyl-ethyl)-phenyl]-D-homo-24-nor-9,10-seco-chola-5,7,10(19)-trien-22-yne-1,3-diol.

30. A compound of formula II:

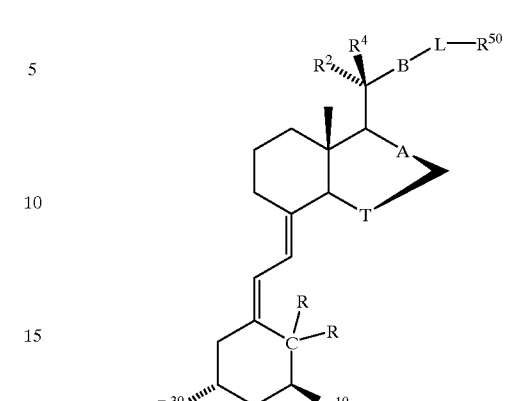

wherein
A, B, T, R, $R^2$, $R^4$ and L are as in claim 1,
$R^{10}$ and $R^{30}$ are H or $OSi(CH_3)_2$-tert-butyl and
$R^{50}$ is $OSi(CH_3)_3$, $OSi(CH_3)_2$-tert-butyl or $C(C_{1-4}$-alkyl$)_2OSi(CH_3)_3$.

31. A pharmaceutical composition which comprises an amount of the compound of formula I

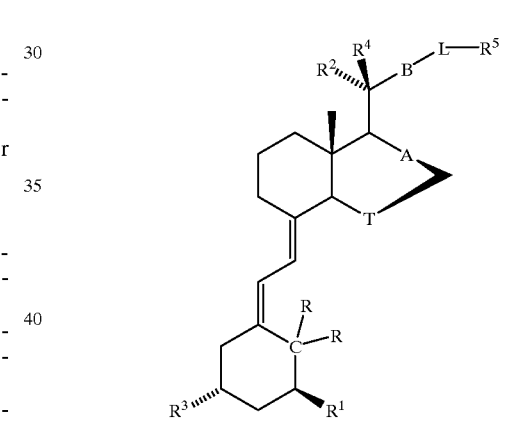

wherein A is a single or double bond; B is $CH_2CH_2$, $CH\equiv CH$, or T is $CH_2$ or $CH_2CH_2$; $CH=CH$ $R^1$ and $R^3$ are H or OH; C(R,R) is $CH_2$ or $C=CH_2$; $R^2$ is $CH_3$ and $R^4$ is H, or $R^2$ is H and $R^4$ is $CH_3$; L is phenyl and $R^5$ is OH or $C(C_{1-4}$-alkyl$)_2OH$ or L—$R^5$ is 2-furyl which is 5-substituted by $C(C_{1-4}$-alkyl$)_2OH$, with the proviso that when L is phenyl; A is a single bond; B is $C\equiv C$; T is $CH_2$; $R^1$ and $R^3$ are OH; C(R,R) is $C=CH_2$; $R^2$ is $CH_3$; $R^4$ is H; and $R^5$ is $C(CH_3)_2OH$; then $R^5$ is in the ortho or para position and a pharmaceutically acceptable carrier.

* * * * *